(12) United States Patent
Strasemeier et al.

(10) Patent No.: US 10,843,455 B2
(45) Date of Patent: *Nov. 24, 2020

(54) METHOD AND APPARATUS FOR CURING INKS PRINTED ON HEAT SENSITIVE ABSORBENT ARTICLE COMPONENTS

(71) Applicant: The Procter & Gamble Company, Cincinnati, OH (US)

(72) Inventors: John Andrew Strasemeier, Aurora, IN (US); Hui Yang, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 277 days.

This patent is subject to a terminal disclaimer.

(21) Appl. No.: 15/911,692

(22) Filed: Mar. 5, 2018

(65) Prior Publication Data

US 2018/0257368 A1  Sep. 13, 2018

Related U.S. Application Data

(60) Provisional application No. 62/467,995, filed on Mar. 7, 2017.

(51) Int. Cl.
*B41F 23/04* (2006.01)
*A61F 13/513* (2006.01)
(Continued)

(52) U.S. Cl.
CPC .... *B41F 23/0409* (2013.01); *A61F 13/15731* (2013.01); *A61F 13/51394* (2013.01);
(Continued)

(58) Field of Classification Search
CPC .......... A61F 13/15731; A61F 13/51394; A61F 13/51496; A61F 13/84; B41F 13/02;
(Continued)

(56) References Cited

U.S. PATENT DOCUMENTS 2,075,189 A   3/1937   Galligan et al.
3,025,199 A   3/1962   Harwood
(Continued)

FOREIGN PATENT DOCUMENTS

DE   202010002859      5/2010
EP   1528907 B1        2/2004
(Continued)

OTHER PUBLICATIONS

U.S. Appl. No. 15/911,635, filed Mar. 5, 2018, Strasemeier.
(Continued)

*Primary Examiner* — David H Banh
(74) *Attorney, Agent, or Firm* — C. Brant Cook

(57) ABSTRACT

Aspects of the present disclosure relate to methods and apparatuses for printing and curing energy curable inks printed on a substrate having an onset temperature $T_{onset}$ (C°). The printing systems may include a printing station and a light source. During operation, the printing station deposits energy curable ink onto a first surface of the substrate to define a printed region, and the light source directs ultraviolet light onto the first surface of the substrate to define an illumination zone on the first surface of the substrate. The substrate is advanced in a machine direction to advance the printed region through the illumination zone to cure the energy curable ink. While the printed region advances through the illumination zone, the ultraviolet light heats the substrate from an initial temperature $T_{in}$ (C°) entering the illumination zone to a maximum temperature $T_{max}$ (C°), wherein $T_{max}$ (C°) ≤ $T_{onset}$ (C°).

20 Claims, 10 Drawing Sheets

(51) Int. Cl.
  *B41M 5/00* (2006.01)
  *B41F 13/02* (2006.01)
  *A61F 13/15* (2006.01)
  *B41M 7/00* (2006.01)
  *A61F 13/84* (2006.01)
  *A61F 13/514* (2006.01)

(52) U.S. Cl.
  CPC ........ *A61F 13/51496* (2013.01); *A61F 13/84* (2013.01); *B41F 13/02* (2013.01); *B41F 23/0479* (2013.01); *B41F 23/0483* (2013.01); *B41M 5/0011* (2013.01); *B41M 7/0081* (2013.01); *A61F 2013/8497* (2013.01)

(58) Field of Classification Search
  CPC .............. B41F 23/0479; B41F 23/0483; B41F 23/0409; B41M 5/0011; B41M 7/0081
  See application file for complete search history.

(56) References Cited

U.S. PATENT DOCUMENTS

| | | |
|---|---|---|
| 3,465,350 A | 9/1969 | Keur et al. |
| 3,465,351 A | 9/1969 | Keur et al. |
| 3,848,594 A | 11/1974 | Buell |
| 3,860,003 A | 1/1975 | Buell |
| 4,033,263 A | 7/1977 | Richmond |
| 4,107,364 A | 8/1978 | Sisson |
| 4,209,563 A | 6/1980 | Sisson |
| 4,321,924 A | 3/1982 | Ahr |
| 4,425,130 A | 1/1984 | DesMarais |
| 4,515,595 A | 5/1985 | Kievit et al. |
| 4,589,876 A | 5/1986 | Van Tilburg |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,834,741 A | 5/1989 | Sabee |
| 4,846,815 A | 7/1989 | Scripps |
| 4,888,231 A | 12/1989 | Angstadt |
| 4,894,060 A | 1/1990 | Nestegard |
| 4,909,803 A | 3/1990 | Aziz et al. |
| 4,940,464 A | 7/1990 | Van Gompel et al. |
| 4,946,527 A | 8/1990 | Battrell |
| 4,950,264 A | 8/1990 | Osborn, III |
| 4,954,371 A * | 9/1990 | Yializis ................... B01D 1/16 392/399 |
| 5,032,461 A * | 7/1991 | Shaw ....................... B05D 1/60 118/50.1 |
| 5,151,092 A | 2/1992 | Buell et al. |
| 5,092,861 A | 3/1992 | Nomura et al. |
| 5,167,897 A | 12/1992 | Weber et al. |
| 5,221,274 A | 6/1993 | Buell et al. |
| 5,246,433 A | 9/1993 | Hasse et al. |
| 5,286,543 A | 2/1994 | Ungpiyakul et al. |
| 5,330,458 A | 7/1994 | Buell et al. |
| 5,359,525 A | 10/1994 | Weyenberg |
| 5,360,420 A | 11/1994 | Cook et al. |
| 5,562,646 A | 10/1996 | Goldman et al. |
| 5,569,234 A | 10/1996 | Buell et al. |
| 5,599,335 A | 2/1997 | Goldman et al. |
| 5,628,097 A | 5/1997 | Benson et al. |
| 5,643,588 A | 7/1997 | Roe et al. |
| 5,669,894 A | 9/1997 | Goldman et al. |
| 5,674,216 A | 10/1997 | Buell et al. |
| 5,702,551 A | 12/1997 | Huber et al. |
| 5,735,840 A | 4/1998 | Kline et al. |
| 5,897,545 A | 4/1999 | Kline et al. |
| 5,916,661 A | 6/1999 | Benson et al. |
| 5,928,212 A | 7/1999 | Kline et al. |
| 5,957,908 A | 9/1999 | Kline et al. |
| 5,968,025 A | 10/1999 | Roe et al. |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,153,209 A | 11/2000 | Vega et al. |
| 6,234,605 B1 | 5/2001 | Hilton |
| 6,251,097 B1 | 6/2001 | Kline et al. |
| 6,309,052 B1 | 10/2001 | Prasad et al. |
| 6,350,071 B1 * | 2/2002 | Conwell ................. B41J 2/325 347/102 |
| 6,410,129 B2 | 6/2002 | Zhang et al. |
| 6,426,444 B2 | 7/2002 | Roe et al. |
| 6,432,098 B1 | 8/2002 | Kline et al. |
| 6,464,316 B1 | 10/2002 | Askeland et al. |
| 6,545,197 B1 | 4/2003 | Muller et al. |
| 6,547,354 B1 | 4/2003 | Askeland et al. |
| 6,586,652 B1 | 7/2003 | Roe et al. |
| 6,617,016 B2 | 9/2003 | Zhang et al. |
| 6,627,787 B1 | 9/2003 | Roe et al. |
| 6,669,618 B2 | 12/2003 | Reising et al. |
| 6,790,798 B1 | 9/2004 | Suzuki et al. |
| 6,801,828 B2 | 10/2004 | Popp et al. |
| 6,811,239 B1 | 11/2004 | Salacz |
| 6,820,022 B2 | 11/2004 | Popp et al. |
| 6,825,393 B2 | 11/2004 | Roe et al. |
| 6,861,571 B1 | 3/2005 | Roe et al. |
| 6,957,884 B2 | 10/2005 | Sharma et al. |
| 7,123,981 B2 | 10/2006 | Dollevoet et al. |
| 8,137,721 B2 | 3/2012 | Wen et al. |
| 8,145,343 B2 | 3/2012 | DeBruler et al. |
| 8,145,344 B2 | 3/2012 | DeBruler et al. |
| 8,217,095 B2 | 7/2012 | Yamaguchi et al. |
| 8,244,393 B2 | 8/2012 | McLaughlin et al. |
| 8,273,066 B2 | 9/2012 | Anderson et al. |
| 8,349,916 B2 | 1/2013 | Kawashima et al. |
| 9,006,509 B2 | 4/2015 | Anderson et al. |
| 9,211,356 B2 | 12/2015 | Gruenbacher et al. |
| 9,238,740 B2 | 1/2016 | Baptista et al. |
| 9,944,073 B2 | 4/2018 | Strasemeier et al. |
| 10,471,738 B2 * | 11/2019 | Strasemeier ...... A61F 13/51496 |
| 2003/0233082 A1 | 12/2003 | Kline et al. |
| 2004/0097895 A1 | 5/2004 | Busam et al. |
| 2004/0158212 A1 | 8/2004 | Ponomarenko et al. |
| 2004/0201660 A1 | 10/2004 | Nishikawa et al. |
| 2005/0015066 A1 | 1/2005 | Anderson et al. |
| 2005/0104946 A1 * | 5/2005 | Siegel ................. B41F 23/0409 347/102 |
| 2006/0033764 A1 | 2/2006 | Aoki |
| 2007/0078427 A1 | 4/2007 | Raycheck et al. |
| 2007/0093769 A1 | 4/2007 | Kline et al. |
| 2007/0126831 A1 | 6/2007 | Suzuki et al. |
| 2007/0273739 A1 | 11/2007 | Rodin |
| 2007/0289484 A1 | 12/2007 | Yamaguchi et al. |
| 2009/0312730 A1 | 12/2009 | LaVon et al. |
| 2010/0064917 A1 | 3/2010 | Blanchard et al. |
| 2010/0233446 A1 | 9/2010 | Kawashima et al. |
| 2010/0310767 A1 * | 12/2010 | Abe ....................... C23C 14/24 427/255.5 |
| 2011/0247508 A1 * | 10/2011 | Baptista ................ B41F 31/027 101/216 |
| 2012/0133716 A1 | 5/2012 | Aizawa et al. |
| 2012/0222576 A1 | 9/2012 | McNeil et al. |
| 2013/0072887 A1 | 3/2013 | LaVon et al. |
| 2013/0192752 A1 * | 8/2013 | Grinberg ................. B32B 37/08 156/275.5 |
| 2013/0211356 A1 | 8/2013 | Nishikawa et al. |
| 2013/0216728 A1 * | 8/2013 | Hurren ................. C23C 14/562 427/551 |
| 2013/0306226 A1 | 11/2013 | Zink et al. |
| 2014/0015887 A1 | 1/2014 | Seccombe |
| 2014/0184681 A1 | 7/2014 | Itogawa |
| 2014/0296420 A1 | 10/2014 | Baptista et al. |
| 2015/0015649 A1 | 1/2015 | Warner et al. |
| 2018/0257398 A1 | 9/2018 | Strasemeier et al. |

(56) References Cited

U.S. PATENT DOCUMENTS

FOREIGN PATENT DOCUMENTS

| | | |
|---|---|---|
| FR | 883712 A | 7/1943 |
| GB | 2142874 A | 1/1985 |

OTHER PUBLICATIONS

14724 PCT International Search Report, dated May 9, 2018, 15 pages.
P&G 14723, All Office Actions, U.S. Appl. No. 15/911,635.

* cited by examiner

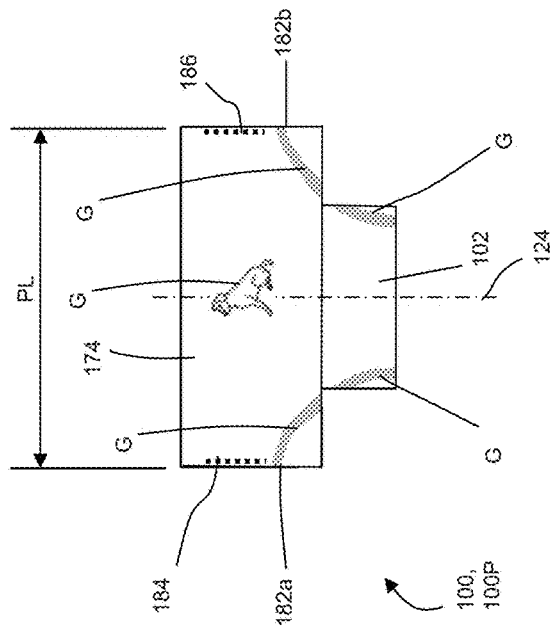
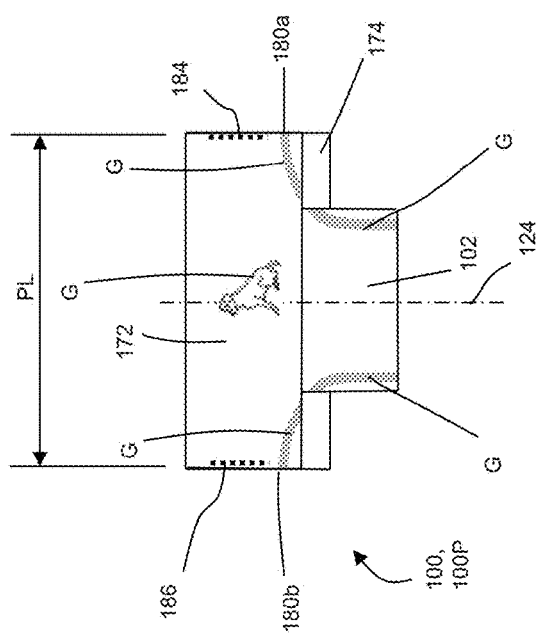
Figure 2C
Figure 2B

METHOD AND APPARATUS FOR CURING INKS PRINTED ON HEAT SENSITIVE ABSORBENT ARTICLE COMPONENTS

FIELD OF THE INVENTION

The present disclosure relates to apparatuses and methods for printing absorbent article component substrates, and more particularly, methods and apparatuses for curing inks printed on heat sensitive substrates.

BACKGROUND OF THE INVENTION

Along an assembly line, diapers and various types of other disposable absorbent articles may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. In some configurations, graphics are printed on individual components and/or continuous webs of material used to assemble the absorbent articles. The graphics may be provided by printing ink on substrate materials by various printing methods, such as flexographic printing, rotogravure printing, screen-printing, inkjet printing, and the like.

In some configurations, printing operations are performed separate to the assembly process, such as for example, printing the substrates offline wherein the printed substrates may be stored until needed for production. For example, printing operations may be accomplished on discrete printing lines, separately from converting lines that are dedicated to manufacturing disposable absorbent articles. After printing on the printing lines, the printed substrates are delivered to the converting lines, such as in a form of continuous webs comprising printed images thereon. In addition to or alternatively to offline printing, graphic printing may be done online during the article assembly process.

Some current printing operations may utilize solvent and/or aqueous based inks to print graphics. However, solvent and/or aqueous based inks may require additional processing steps after the ink is printed. Such additional process steps may include drying operations that may require evaporation of some ingredient of the inks, such as a solvent or a thinner. External heating systems may also be required to complete these drying steps. As such, the required drying steps may be difficult to complete at relatively high manufacturing and/or printing speeds to ensure printed inks are adequately dried before subjecting printed substrates to additional processing operations. In order to avoid the drying steps that may be required when printing with solvent and/or aqueous based inks, some printing operations may utilize wax based inks that may have a solid state at room temperature. Before printing, the wax based inks may be heated and converted to a liquid state. The wax based inks may then be printed onto a substrate while in the liquid state. The printed wax based ink then solidifies when cooled. However, wax based inks may require specific types of printing devices that are particularly configured to print liquids having the properties of wax based inks. Additional heating and fluid handling systems may be required to ensure the wax based inks are maintained in a liquid state before being applied to a substrate. In addition, it may be difficult to adequately cool the ink at relatively high manufacturing and/or printing speeds to ensure printed inks are adequately solidified before subjecting printed substrates to additional processing operations.

In an attempt to overcome the aforementioned drawbacks related to printing with wax based inks and/or other inks that require drying operations, some printing operations may utilize energy curable inks that are cured by chemical reactions. Examples of energy curable inks may include ultraviolet curable inks. Unlike inks that need to be dried, once energy curable ink is deposited in a liquid state on a substrate, the ink may be cured and solidified by subjecting the ink to a radiation source, such as ultraviolet light. During the curing process, the radiation source imparts energy to the ink. And the energy imparted to the ink from the radiation source is proportional to the intensity of the radiation directed at the ink and the time during which ink is subjected to the radiation. The amount of energy required to cure an ink will vary based on a number of different factors. For example, for an ink deposited in a particular area of a substrate, the amount of energy required to cure the ink deposited in that area will increase or decrease along with the amount of ink deposited in that area. Thus, the intensity of the radiation and/or the time at which the ink is subjected to the intensity may be increased or decreased depending on the amount of ink in a particular area.

Some of the radiation used to cure the ink may also be absorbed by the substrate and converted into heat energy. As such, curing ink printed on heat sensitive substrates, such as nonwovens and films, may present various challenges. For example, in some configurations where printing is performed online during an article assembly process, a printed substrate may be required to advance past the radiation source at a relatively high rate of speed. As such, the time during which printed ink is exposed to radiation may be relatively short. As discussed above, in order to cure the ink in a relatively short period of time, the intensity of the radiation may need to be increased to relatively high levels. However, if the intensity of the radiation is too high over a period of time, the heat energy created in the substrate by the radiation may destroy and/or damage the advancing substrate.

Consequently, there remains a need to configure ultraviolet curable ink printing systems to help ensure that ink printed on a substrate can be cured at relatively high speeds without damaging the substrate.

SUMMARY OF THE INVENTION

In one form, a method for printing comprises the steps of: providing a substrate extending in a machine direction, the substrate comprising a first surface and an opposing second surface and defining a width in a cross direction; depositing energy curable ink onto the first surface of the substrate to define a printed region; directing ultraviolet light from a light source onto the first surface of the substrate to define an illumination zone extending for a length, L (m), in the machine direction on the first surface of the substrate; advancing the printed region through the illumination zone; curing energy curable ink advancing through the illumination zone with ultraviolet light traveling from the light source; and removing heat energy from the substrate.

In another form, a method for printing comprises the steps of: providing a nonwoven substrate extending in a machine direction, the substrate comprising a first surface and an opposing second surface and defining a width in a cross direction, the substrate comprising an onset temperature $T_{onset}$ (C°); depositing energy curable ink onto the first surface of the nonwoven substrate to define a printed region;

directing ultraviolet light from a light source onto the first surface of the nonwoven substrate to define an illumination zone extending for a length, L (m), in the machine direction on the first surface of the substrate; advancing the printed region through the illumination zone at a speed, S (m/s), such that the ultraviolet light heats the nonwoven substrate from an initial temperature $T_{in}$ (C°) entering the illumination zone to a maximum temperature $T_{max}$ (C°), wherein $T_{max}$ (C°)≤$T_{onset}$ (C°) in the illumination zone; and curing energy curable ink advancing through the illumination zone with ultraviolet light traveling from the light source.

In yet another form, an apparatus for printing a substrate extending in a machine direction and comprising a first surface and an opposing second surface and defining a width in a cross direction comprises: a supply of energy curable ink; a printing station positioned to deposit energy curable ink from the supply onto the first surface of the substrate; and a curing apparatus for curing the energy curable ink on the substrate, the curing apparatus comprising: a light source positioned to direct ultraviolet light toward the first surface of the substrate at a location downstream in the machine direction from the printing station, wherein the ultraviolet light source comprises a wavelength, and a chill roll comprising an outer circumferential surface positioned to support the second surface of the substrate, wherein the chill roll is adapted to remove heat energy imparted to the substrate from the curing apparatus.

BRIEF DESCRIPTION OF THE DRAWINGS

FIG. 2B is a front view of the absorbent article of FIG. 2A.

FIG. 2C is a rear view of the absorbent article of FIG. 2A.

DETAILED DESCRIPTION OF THE INVENTION

Figure 1A:
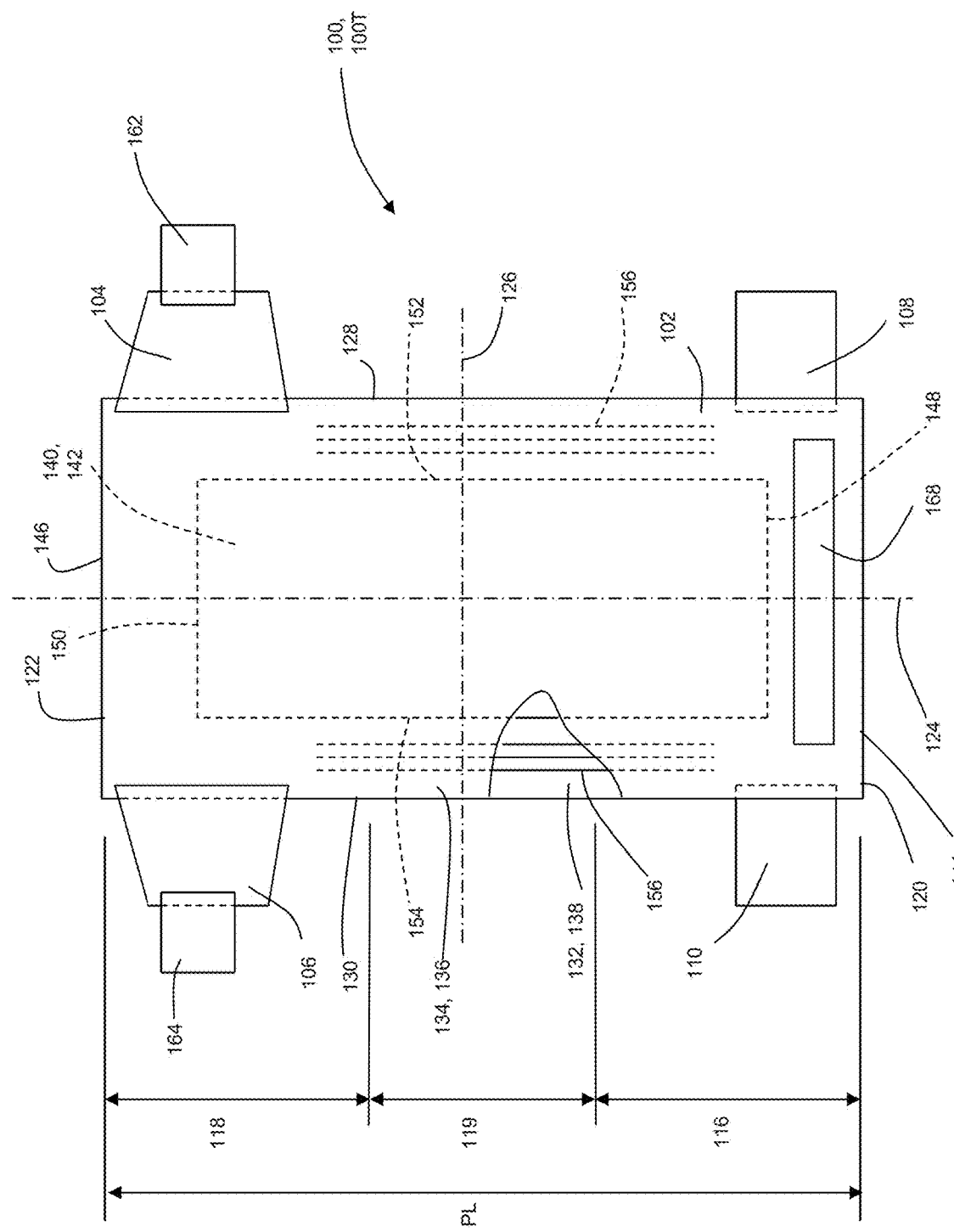
FIG. 1A is a partially cut away plan view of an absorbent article in the form of a taped diaper that may include one or more substrates printed in accordance with the present disclosure with the portion of the diaper that faces away from a wearer oriented towards the viewer.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082 A1.

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. In some configurations, a nonwoven may comprise a polyolefin based nonwoven, including but not limited to nonwovens having polypropylene fibers and/or polyethylene fibers and/or bicomponent fibers comprising a polyolefin. Nonlimiting examples of suitable fibers include spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers as known in the art, and workable combinations thereof. Nonwovens do not have a woven or knitted filament pattern. It is to be appreciated that nonwovens having various basis weights can be used in accordance with the methods herein. For example, some nonwovens may have a basis weight of at least about 8 gsm, 12 gsm, 16 gsm, 20 gsm, 25 gsm, 25 gsm, 40 gsm, or 65 gsm. Some nonwovens may have basis weight of about 8 gsm to about 65 gsm, specifically reciting all 1 gsm increments within the above-recited ranges and all ranges formed therein or thereby.

It is to be appreciated that films having various basis weights can be used in accordance with the methods herein. For example, some films may have a basis weight of at least about 8 gsm, 12 gsm, 16 gsm, 20 gsm, 25 gsm, 25 gsm, 40 gsm, or 60 gsm. Some films may have basis weight of about 8 gsm to about 60 gsm, specifically reciting all 1 gsm increments within the above-recited ranges and all ranges formed therein or thereby.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

Aspects of the present disclosure relate to methods and apparatuses for printing absorbent article substrates, and in particular, methods and apparatuses for printing and curing energy curable inks printed on substrates. The substrate extends in a machine direction MD, defines a width in a cross direction CD, and includes a first surface and an opposing second surface. The substrate also has an onset temperature $T_{onset}$ (C°). As discussed in more detail below, printing systems according to the present disclosure may include a printing station and a light source. During operation, the printing station deposits energy curable ink onto the first surface of the substrate to define a printed region. And the light source directs ultraviolet light onto the first surface of the substrate to define an illumination zone extending for a length in the machine direction on the first surface of the substrate. The substrate is advanced in the machine direction to advance the printed region through the illumination zone to cure the energy curable ink. While the printed region advances through the illumination zone at a speed, the ultraviolet light heats the substrate from an initial temperature $T_{in}$ (C°) entering the illumination zone to a maximum temperature $T_{max}$ (C°), wherein $T_{max}$ (C°)≤$T_{onset}$ (C°). In some configurations, the printing system may include a cooling apparatus adjacent the advancing substrate, wherein the cooling apparatus removes heat energy from the substrate while the printed region advances through the illumination zone. The cooling apparatus may also be configured to remove heat energy from the substrate before and/or after the printed region advances through the illumination zone. As such, the printing systems herein may be configured and operated to help ensure that energy curable ink is cured at relatively high speeds without damaging the substrate by overheating the substrate.

Figure 1B:
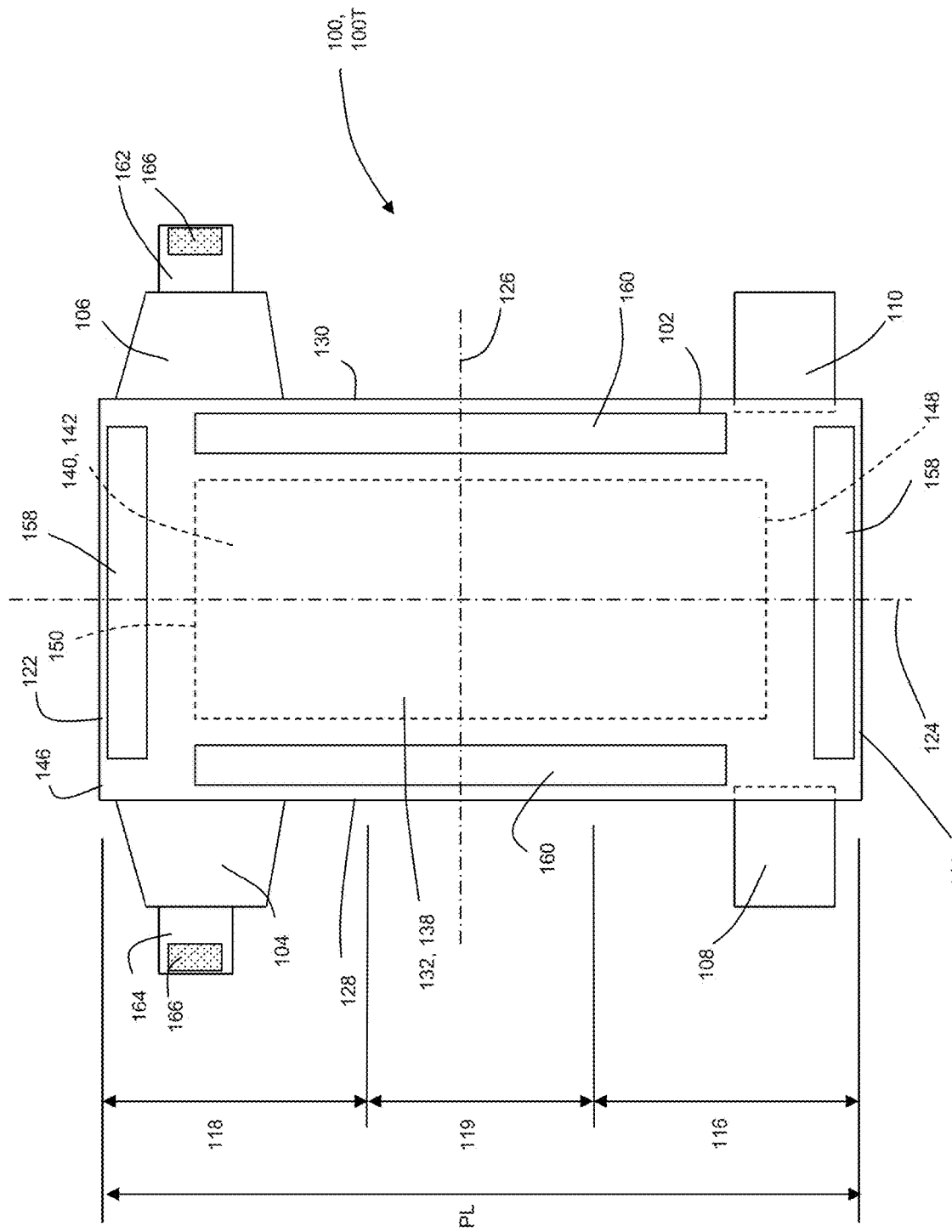
FIG. 1B is a plan view of the absorbent article of FIG. 1A that may include one or more substrates printed in accordance with the present disclosure with the portion of the diaper that faces toward a wearer oriented towards the viewer.

It is to be appreciated that the systems and methods disclosed herein are applicable to work with various types of converting processes and/or machines, such as for example, absorbent article manufacturing, packaging, and/or printing processes. The methods and apparatuses are discussed below in the context of manufacturing diapers. And for the purposes of a specific illustration, FIGS. 1A and 1B show an example of an absorbent article 100 that may be assembled in accordance with the methods and apparatuses disclosed herein. In particular, FIG. 1A shows one example of a plan view of an absorbent article 100 configured as a taped diaper 100T, with the portion of the diaper that faces away from a wearer oriented towards the viewer. And FIG. 1B shows a plan view of the diaper 100 with the portion of the diaper that faces toward a wearer oriented towards the viewer. The taped diaper 100T shown in FIGS. 1A and 1B includes a chassis 102, first and second rear side panels 104 and 106; and first and second front side panels 108 and 110.

As shown in FIGS. 1A and 1B, the diaper 100 and the chassis 102 each include a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be 1/3 of the length of the absorbent article 100. The absorbent article may also include a laterally extending front waist edge 120 in the front waist region 116 and a longitudinally opposing and laterally extending back waist edge 122 in the back waist region 118. To provide a frame of reference for the present discussion, the diaper 100T in FIGS. 1A and 1B is shown with a longitudinal axis 124 and a lateral axis 126. The longitudinal axis 124 may extend through a midpoint of the front waist edge 120 and through a midpoint of the back waist edge 122. And the lateral axis 126 may extend through a midpoint of a first longitudinal or right side edge 128 and through a midpoint of a second longitudinal or left side edge 130.

As shown in FIGS. 1A and 1B, the diaper 100 includes an inner, body facing surface 132, and an outer, garment facing surface 134. And the chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs, an elastic waist region, and/or flaps, e.g., side panels and/or ears, to enhance the fits around the legs and waist of the wearer, to enhance the fit around the legs of the wearer.

As shown in FIGS. 1A and 1B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 1A, the laterally extending end edges 144 and 146 may form a portion of the laterally extending front waist edge 120 in the front waist region 116 and a portion of the longitudinally opposing and laterally extending back waist edge 122 in the back waist region 118. The distance between the first lateral end edge 144 and the second lateral end edge 146 may define a pitch length, PL, of the chassis 102. When the diaper 100 is worn on the lower torso of a wearer, the front waist edge 120 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper 100 may also include an absorbent assembly 140 that is joined to the chassis 102. As shown in FIGS. 1A and 1B, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1.

As previously mentioned, the diaper 100 may also include elasticized leg cuffs 156 and an elasticized waistband 158. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; and U.S. Patent Publication No. 2009/0312730 A1.

The elasticized waistband 158 may provide improved fit and containment and may be a portion or zone of the diaper 100 that may elastically expand and contract to dynamically fit a wearer's waist. The elasticized waistband 158 may extend longitudinally inwardly from the waist edges 120, 122 of the diaper toward the lateral edges 148, 150 of the absorbent core 142. The diaper 100 may also include more than one elasticized waistband 158, for example, having one waistband 158 positioned in the back waist region 118 and one waistband 158 positioned in the front wait region 116, although other embodiments may be constructed with a single elasticized waistband 158. The elasticized waistband 158 may be constructed in a number of different configurations including those described in U.S. Pat. Nos. 4,515,595 and 5,151,092. In some embodiments, the elasticized waistbands 158 may include materials that have been "prestrained" or "mechanically prestrained" (subjected to some degree of localized pattern mechanical stretching to permanently elongate the material). The materials may be prestrained using deep embossing techniques as are known in the art. In some embodiments, the materials may be prestrained by directing the material through an incremental mechanical stretching system as described in U.S. Pat. No. 5,330,458. The materials are then allowed to return to their substantially untensioned condition, thus forming a zero strain stretch material that is extensible, at least up to the point of initial stretching. Examples of zero strain materials are disclosed in U.S. Pat. Nos. 2,075,189; 3,025,199; 4,107,364; 4,209,563; 4,834,741; and 5,151,092.

As shown in FIG. 1B, the chassis 102 may include longitudinally extending and laterally opposing side flaps 160 that are disposed on the interior surface 132 of the chassis 102 that faces inwardly toward the wearer and contacts the wearer. Each side flap may have a proximal edge. The side flaps may also overlap the absorbent assembly 140, wherein the proximal edges extend laterally inward of the respective side edges of the absorbent assembly 152 and 154. In some configurations, the side flaps may not overlap the absorbent assembly. It is to be appreciated that the side flaps may be formed in various ways, such as for example, by folding portions of the chassis 102 laterally inward, i.e., toward the longitudinal axis 124, to form both the respective side flaps and the side edges 128 and 130 of the chassis 102. In another example, the side flaps may be formed by attaching an additional layer or layers to the chassis at or adjacent to each of the respective side edges and of the chassis. Each of the side flaps may be joined to the interior surface 132 of the chassis and/or the absorbent assembly in side flap attachment zones in the front waist region 116 and in side flap attachment zones in the back waist region 118. The side flaps may extend to the same longitudinal extent as the absorbent article or alternatively the side flaps may have a longitudinal extent that is less than the absorbent article.

Taped diapers may be manufactured and provided to consumers in a configuration wherein the front waist region and the back waist region are not fastened, pre-fastened, or connected to each other as packaged, prior to being applied to the wearer. For example, the taped diaper 100 may be folded about a lateral centerline with the interior surface 132 of the first waist region 116 in surface to surface contact with the interior surface 132 of the second waist region 118 without fastening or joining the waist regions together. The rear side panels 104 and 106 and/or the front side panels 108 and 110 may also be folded laterally inward toward the inner surfaces 132 of the waist regions 116 and 118.

The diaper 100 may also include various configurations of fastening elements to enable fastening of the front waist region 116 and the back waist region 118 together to form a closed waist circumference and leg openings once the diaper is positioned on a wearer. For example, as shown in FIGS. 1A and 1B, the diaper 100 may include first and second fastening members 162, 164, also referred to as tabs, connected with the first and second rear side panels 104, 106, respectively. The diaper may also include first and second front side panels 108, 110, that may or may not include fastening members.

With continued reference to FIGS. 1A and 1B, each side panel 104, 106 and/or fastening member 162 and 164 may form a portion of or may be permanently bonded, adhered or otherwise joined directly or indirectly to the chassis 102 laterally inward from the side edge 128 and 130, in one of the front waist region 116 or the back waist region 118. Alternatively, the fastening members 162, 164 may form a portion of or may be permanently bonded, adhered or otherwise joined directly or indirectly to the first and second rear panels 104, 106 at or adjacent the distal edge of the panel and/or the first and second front side panels 108 and 110 at or adjacent the distal edge of the side panel. It is to be appreciated that the fastening members and/or side panels may be assembled in various ways, such as disclosed for example, in U.S. Pat. No. 7,371,302. The fastening members 162, 164 and/or side panels 104, 106, 108, 110 may also be permanently bonded or joined at or adjacent the side edges 128 and 130 of the chassis 102 in various ways, such as for example, by adhesive bonds, sonic bonds, pressure bonds, thermal bonds or combinations thereof, such as disclosed for example, U.S. Pat. No. 5,702,551.

Referring now to FIG. 1B, the first fastening member 162 and/or the second fastening member 164 may include various types of releasably engageable fasteners. The first and second fastening members 162 and/or 164 may also include various types of refastenable fastening structures. For example, the first and second fastening members 162 and 164 may include mechanical fasteners, 166, in the form of hook and loop fasteners, hook and hook fasteners, macrofasteners, buttons, snaps, tab and slot fasteners, tape fasteners, adhesive fasteners, cohesive fasteners, magnetic fasteners, hermaphroditic fasteners, and the like. Some examples of fastening systems and/or fastening members 162, 164 are discussed in U.S. Pat. Nos. 3,848,594; 4,662,875; 4,846,815; 4,894,060; 4,946,527; 5,151,092; 5,221,274; 6,251,097; 6,669,618; 6,432,098; and U.S. Patent Publication Nos. 2007/0078427 A1 and 2007/0093769 A1.

As previously mentioned, the fastening members 162 and 164 may be constructed from various materials and may be constructed as a laminate structure. The fastening members 162 and 164 may also be adapted to releasably and/or refastenably engage or connect with another portion of the diaper 100. For example, as shown in FIG. 1A, the diaper 100 may include a connection zone 168, sometimes referred to as a landing zone, in the first waist region 116. As such, when the taped diaper 100 is placed on a wearer, the fastening members 162 and 164 may be pulled around the waist of the wearer and connected with the connection zone 168 in the first waist region 116 to form a closed waist circumference and a pair of laterally opposing leg openings.

Figure 1C:
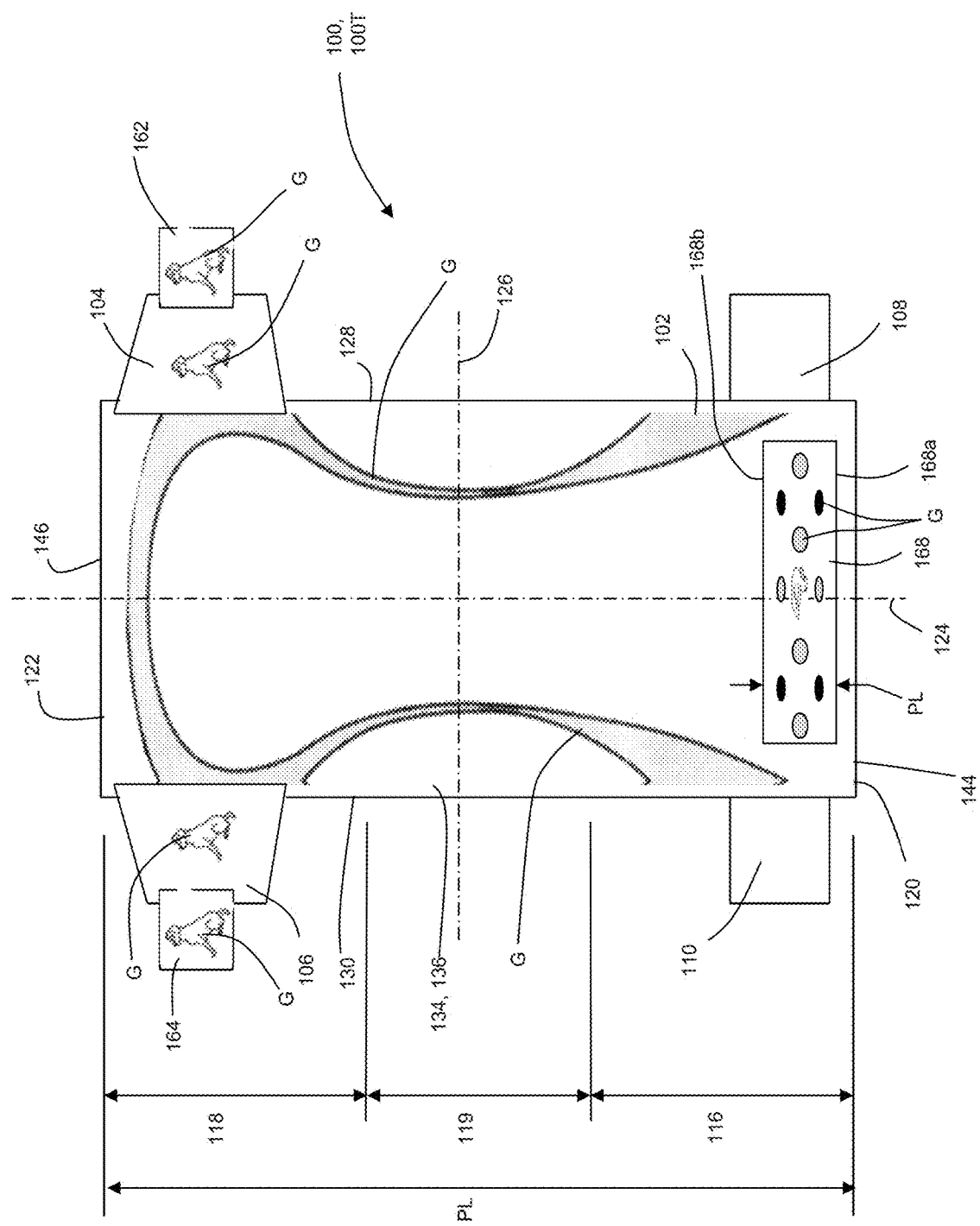
FIG. 1C is a plan view of a diaper with graphics on a backsheet, side panels, and a connection zone.

It is to be appreciated that the connection zone may be constructed from a separate substrate that is connected with the chassis 102 of the taped diaper, such as shown in FIG. 1C. As such, the connection zone 168 may have a pitch length PL defined by a distance extending between a first lateral end edge 168a and the second lateral end edge 168b. In some embodiments, the connection zone may be integrally formed as part of the backsheet 136 of the diaper 100 or may be formed as part of the first and second front panels 108, 110, such as described in U.S. Pat. Nos. 5,735,840 and 5,928,212.

Figure 2A:
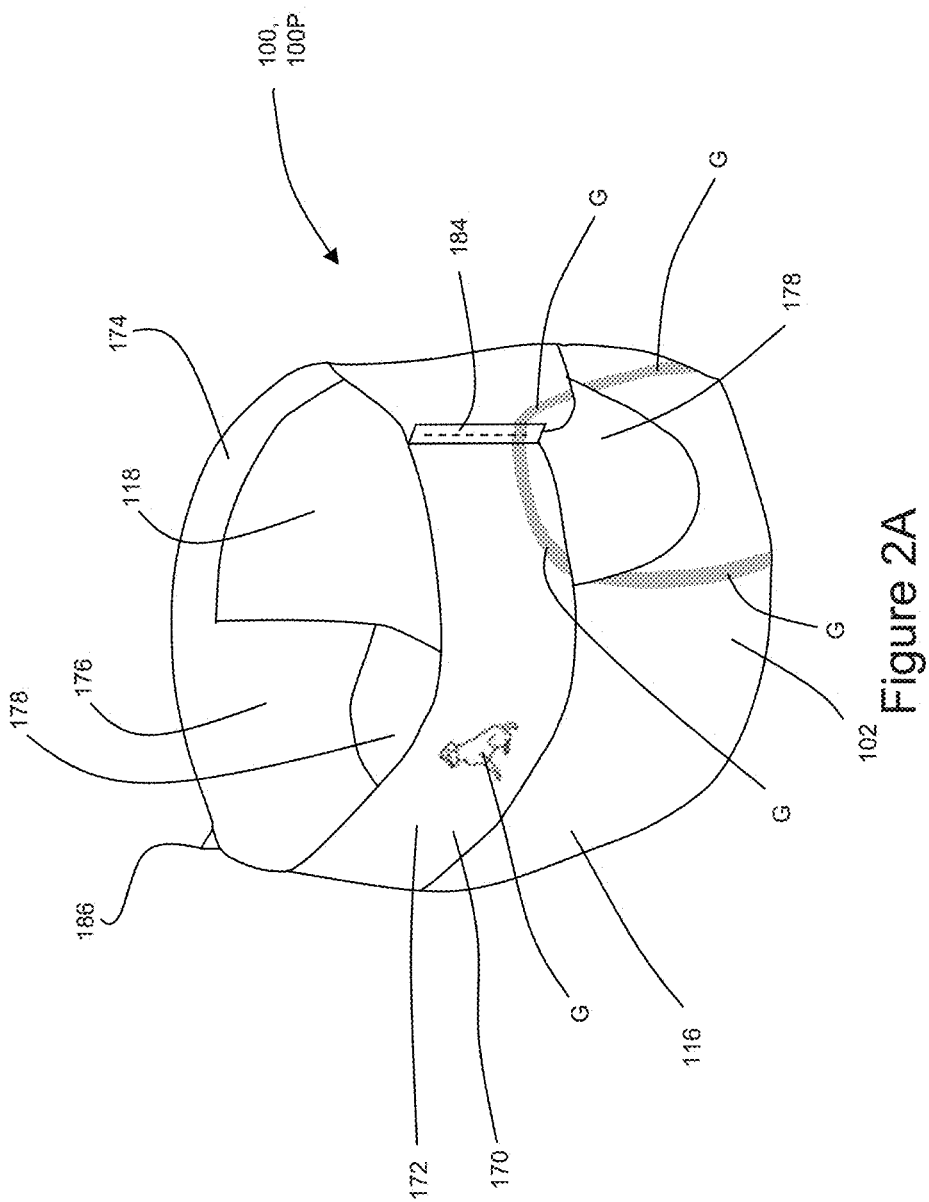
FIG. 2A is a front perspective view of an absorbent article in the form of a diaper pant with graphics on a chassis and front and rear belts.

As previously mentioned, absorbent articles 100 may also be configured as diaper pants 100P having a continuous perimeter waist opening and continuous perimeter leg openings. For example, FIG. 2A shows a perspective view of an absorbent article 100 in the form of a diaper pant 100P in a pre-fastened configuration, and FIGS. 2B-2C show front and rear plan views of the diaper pant 100P. The diaper pant 100P may include a chassis 102 such a discussed above with reference to FIG. 1A and a ring-like elastic belt 170 such as shown in FIG. 2A. In some embodiments, a first elastic belt 172 and a second elastic belt 174 are bonded together to form the ring-like elastic belt 170. As such, diaper pants may be manufactured with the ring-like elastic belt 174 and provided to consumers in a configuration wherein the front waist region 116 and the back waist region 118 of the chassis 102 are connected to each other as packaged, prior to being applied to the wearer. As such, diaper pants may have a continuous perimeter waist opening 176 and continuous perimeter leg openings 178 such as shown in FIG. 2A.

As previously mentioned, the ring-like elastic belt 170 may be defined by a first elastic belt 172 connected with a second elastic belt 174. As shown in FIGS. 2A-2C, the first elastic belt 172 extends between a first longitudinal side edge 180a and a second longitudinal side edge 180b. And the second elastic 174 belt extends between a first longitudinal side edge 182a and a second longitudinal side edge 182b. The distance between the first longitudinal side edge 180a and the second longitudinal side edge 180b defines a pitch length, PL, of the first elastic belt 172, and the distance between the first longitudinal side edge 182a and the second longitudinal side edge 182b defines the pitch length, PL, of the second elastic belt 174. The first elastic belt is connected with the first waist region 116 of the chassis 102, and the second elastic belt 108 is connected with the second waist region 116 of the chassis 102. As shown in FIGS. 2A-2C, opposing end regions of the first elastic belt 172 are connected with opposing end regions of the second elastic belt 174 at a first side seam 184 and a second side seam 186 to define the ring-like elastic belt 170 as well as the waist opening 176 and leg openings 178. It is to be appreciated that the ring-like elastic belt may be formed by joining a first elastic belt to a second elastic belt with permanent side seams or with openable and reclosable fastening systems disposed at or adjacent the laterally opposing sides of the belts.

As previously mentioned, absorbent articles may be assembled with various components that may be printed off-line, before assembly, or on-line, as part of the assembly process. As such, the absorbent articles herein may include graphics printed on various components. Thus, in the context of the previous discussion, the apparatuses and methods herein may be used to print substrates configured as continuous substrates and/or discrete components of an absorbent article 100, either off-line or on-line. For example, the apparatuses and methods herein may be utilized in to print graphics on any of the topsheet 138; backsheet 136; absorbent core 140; leg cuffs 156; waist feature 158; side panels 104, 106, 108, 110; connection zones 168; fastening elements 162, 164, 166, and/or belts before, during, and/or after the manufacture of an absorbent article 100. For example, the backsheet 136 of the taped diaper 100T shown in FIG. 1C includes graphics G that may be printed before, during, and/or after assembly. The connection zone 168 and the side panels 104, 106, and fastening members 162, 164 shown in FIG. 1C may also include graphics G printed before, during, and/or after assembly. In yet another example, the front belt 172 and rear belt 174 of the diaper pant 100P may include graphics G printed before, during, and/or after assembly. As discussed in more detail below, the systems and methods herein may be utilized to print such graphics before, during, and/or after assembly.

Figure 3:
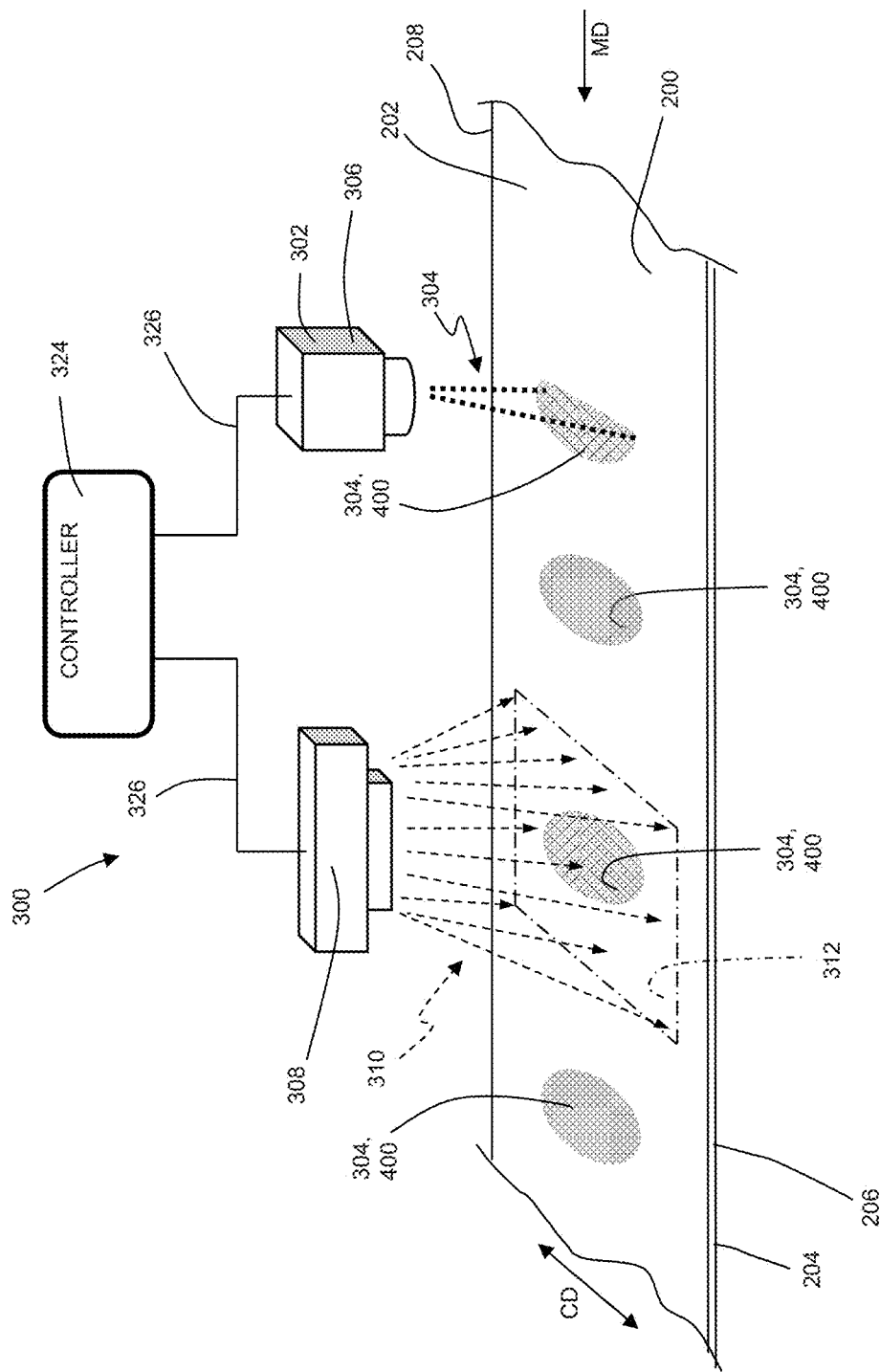
FIG. 3 is a schematic side view of a printing system for printing an advancing substrate.

It is to be appreciated that the printing systems and methods disclosed herein are applicable to work with various types of converting processes and/or machines. For example, FIG. 3 shows a schematic representation of a converting process including a printing apparatus or system 300 for printing graphics on a substrate 200 advancing in a machine direction MD. The substrate 200 may be a continuous substrate and may include a first surface 202 and an opposing second surface 204. The substrate 200 may also define a width W extending in the cross direction CD between a first longitudinal side edge 206 and a second longitudinal side edge 208.

As shown in FIGS. 3-6, the printing system 300 may include a printing station 302. During operation, the substrate 200 advances in the machine direction MD a speed, S (m/s). In turn, the printing station 302 deposits energy curable ink 304 onto the first surface 202 of the advancing substrate 200 to define a printed region 400. It is to be appreciated that the substrates 200 herein may be advanced in the machine direction MD at various speeds S. For example, the substrate 200 may be configured to advance in the machine direction MD at a speed S of about 0.5 meters/second (m/s) to about 15 m/s, specifically reciting all 1 m/s increments within the above-recited ranges and all ranges formed therein or thereby. In some configurations, the speed S is equal to or greater than about 6 m/s. As shown in FIG. 3, the printing system 300 also includes a light source 308 that directs ultraviolet light 310 onto the first surface 202 of the substrate 200 to define an illumination zone 312 extending in the machine direction MD on the first surface 202. The printed region 400 advances through the illumination zone 312. In turn, energy curable ink 304 advancing through the illumination zone 312 is cured with the ultraviolet light 310 traveling from the light source 308. As discussed in more detail below, the printing system 300 may also be configured to remove heat energy from the substrate 200 before, during, and/or after the printed region 400 advances through the illumination zone 312.

It is to be appreciated that the advancing substrate 200 may be supported in various ways to mitigate movement while energy curable ink 304 is being deposited and/or cured on the substrate 200. For example, the second surface 204 of the substrate 200 may be supported by a conveyor having a series of rollers, an advancing belt, and/or a rotating drum. It is to be appreciated that the printed substrate 200 may be subject to additional manufacturing operations, such as combining and/or cutting operations, during assembly of a product.

It is also to be appreciated that the substrate 200 may be configured in various ways. For example, the substrate 200 herein may be configured as a single nonwoven substrate or a single film substrate that defines both the first surface 202 and the second surface 204. It is also to be appreciated that the substrate 200 herein may be configured as a laminate including various layers of substrates bonded together, wherein a nonwoven substrate layer defines the first surface 202 and another substrate layer defines the second surface 204. For example, the substrate 200 may include a nonwoven substrate layer or a film substrate layer that defines the first surface 202 and a second substrate layer defining the second surface 204, wherein the second substrate layer may include a nonwoven or a film.

The printed region 400 is generically represented herein as an oval shape on the first surface 202 of the substrate 200. It is to be appreciated that the printing station 302 can be configured to print a plurality of printed regions arranged along the machine direction MD and/or cross direction of the substrate 200. It is also to be appreciated that a single printed region 400 or a plurality of printed regions 400 may form a graphic. As used herein, the term "graphic" refers to images or designs that are constituted by a figure (e.g., a line(s)), a symbol or character, a color difference or transition of at least two colors, or the like. A graphic may include an aesthetic image or design that can provide certain benefit(s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

It is to be appreciated that the printing station 302 may be configured in various ways and may include various types of printing accessories. For example, the printing station 302 may include a printer 306, which be configured in various ways. In some configurations, the printing station 302 may also include a corona treater, which may be positioned upstream of the printer 306. The corona treater may be configured to increase the surface energy of the surface of the substrate 200. For example, the corona treater may be configured to increase the surface energy of the surface to be printed to about 42 dynes/cm. In some configurations, the printer 306 may be in the form of a flexographic printer. In particular, a flexographic printer may utilize printing plates made of rubber or plastic with a slightly raised image thereon. The inked plates are rotated on a cylinder which transfers the image to the sheet. Some configurations may include a printer 306 in the form of a gravure printer. Gravure printing may utilize an image etched on the surface of a metal plate. The etched area is filled with ink and the plate is rotated on a cylinder that transfers the image to the substrate. In some configurations, printing devices such as disclosed in U.S. Patent Publication No. 2012/0222576 A1 may be used. In some configurations, the printer 306 may include various quantities of non-contact printheads arranged and/or configured in various ways to deposit inks onto the advancing substrate 200 to create printed regions 400. For example, in some embodiments, the printheads herein may be configured as inkjet printheads. Inkjet printing is a non-impact dot-matrix printing technology in which droplets of ink are jetted from a small orifice in the printhead directly to a specified position on a substrate to create a graphic. The inkjet printheads herein may be configured to perform different types of inkjet printing, such as for example, "drop-on-demand" and "continuous" inkjet printing.

With "continuous" inkjet printing processes, an ink is supplied under pressure to an inkjet nozzle and forced out through a small orifice. Prior to passing out of the nozzle, the pressurized ink stream proceeds through a ceramic crystal, which is subjected to an electric current. The electric current causes a piezoelectric vibration equal to the frequency of an AC electric current. The vibration, in turn, generates the ink droplets from the unbroken ink stream. As such, the ink stream breaks up into a continuous series of drops which are equally spaced and of equal size. Surrounding the jet, at a point where the drops separate from the fluid stream in a charge electrode, a voltage is applied between the charge electrode and the drop stream. When the drops break off from the stream, each drop carries a charge proportional to the applied voltage at the instant at which it breaks off. By varying the charge electrode voltages at the same rate as drops are produced, it is possible to charge every drop to a predetermined level. The drop stream passes between two deflector plates which are maintained at a constant potential that deflects a drop towards one of the plates by an amount proportional to the charge carried. Drops that are uncharged are undeflected and collected into a gutter to be recycled to the ink nozzle. Those drops which are charged, and hence deflected, impinge on a substrate traveling at a high speed at right angles to the direction of drop deflection. By varying the charge on individual drops, a desired pattern can be printed.

With "drop-on-demand" inkjet printing processes, an ink is forced under pressure from the printhead through a relatively small orifice in the form of minute droplets by rapid pressure impulses. In some configurations, the orifice may have a diameter of about 0.0024 inches (5-50 microns). The rapid pressure impulses may be generated in the printhead by either expansion of a piezoelectric crystal vibrating at a high frequency or volatilization of a volatile composition (e.g. solvent, water, propellant) within the ink by rapid heating cycles. The piezoelectric crystal expansion causes the ink to pass through the orifice as minute droplets in proportion to the number of crystal vibrations. Thermal inkjet printers employ a heating element within the print head to volatilize a portion of the composition that propels the vast majority of fluid through the orifice nozzle to form droplets in proportion to the number of on-off cycles for the heating element. The ink is forced out of the nozzle when needed to print a spot on a substrate as part of a desired image. The minute droplets may also be energized to achieve an electrical charge and deflected as in the continuous inkjet printing process discussed above. Various inkjet printing processes are more particularly described in U.S. Pat. Nos. 3,465,350; 3,465,351; and 9,211,356.

Although the printing station 302 may include a single printhead, it is to be appreciated that printing stations 302 herein may be configured with more than one printhead arranged in the cross direction CD and/or machine direction MD. In some configurations, the printing stations 302 herein may include backup printheads, such as disclosed in U.S. Pat. No. 6,811,239. It is also to be appreciated that the printheads may be configured to print inks having the same colors or different colors. For example, a first ink may comprise a first color, and a second ink may comprise a second color different from the first color. In another example, a first ink may comprise a first color, and a second ink may comprise a second color that is the same as the first color. In addition, the printheads herein may be configured to perform single color, multi-color, halftone, and process printing.

"Halftone" or "halftoning" as used herein, sometimes referred to as "screening," is a printing technique that allows for less-than-full saturation of the primary colors. In halftoning, relatively small dots of each primary color are printed in a pattern small enough such that the average human observer perceives a single color. For example, magenta printed with a 20% halftone will appear to the average observer as the color pink. The reason for this is because, without wishing to be limited by theory, the average observer may perceive the tiny magenta dots and white paper between the dots as lighter, and less saturated, than the color of pure magenta ink. A "base color," as used herein, refers to a color that is used in the halftoning printing process as the foundation for creating additional colors. In some non-limiting embodiments, a base color is provided by a colored ink. Non-limiting examples of base colors may selected from the group consisting of: cyan, magenta, yellow, black, red, green, and blue-violet. "Black", as used herein, refers to a color and/or base color which absorbs wavelengths in the entire spectral region of from about 380 nm to about 740 nm. "Cyan", as used herein, refers to a color and/or base color which have a local maximum reflectance in the spectral region of from about 390 nm to about 570 nm. In some embodiments, the local maximum reflectance is between the local maximum reflectance of the blue or blue-violet and green local maxima. "Magenta", as used herein, refers to a color and/or base color which have a local maximum reflectance in the spectral region of from about 390 nm to about 490 nm and 621 nm to about 740 nm. "Yellow", as used herein, refers to a color and/or base color which have a local maximum reflectance in the spectral region of from about 571 nm to about 620 nm.

"Process Printing," as used herein, refers to the method of providing color prints using at least three of the primary of colors cyan, magenta, yellow and black. Each layer of color is added over a base substrate. In some embodiments, the base substrate is white or off-white in color. With the addition of each layer of color, certain amounts of light are absorbed (those of skill in the printing arts will understand that the inks actually "subtract" from the brightness of the white background), resulting in various colors. CMY (cyan, magenta, yellow) are used in combination to provide additional colors. Non-limiting examples of such colors are red, green, and blue. K (black) is used to provide alternate shades and pigments. One of skill in the art will appreciate that CMY may alternatively be used in combination to provide a black-type color.

An "ink" is a liquid containing coloring matter, for imparting a particular hue to a substrate. An ink may include dyes, pigments, organic pigments, inorganic pigments, and/or combinations thereof. It is also to be appreciated that the printing systems 300 herein may be configured to operate with various types of energy curable inks. Unlike traditional inks that dry when exposed to heat or ambient air for a given time, energy curable inks undergo a photochemical reaction when exposure to intense light or energy waves. For example, the energy curable inks 304 herein may be configured as ultraviolet curable inks. Ultraviolet curable inks are cured by exposure to ultraviolet light. Examples of such ultraviolet curable inks are available from Kao Collins Inc. of Cincinnati, Ohio under the following product codes/categories: Jet LED Platform; PUC250454 cyan; PUC261754 cyan; PUC262154 LIGHT cyan; PUY250654 yellow; PUY261954 yellow; PUM250554 magenta; PUM261854 magenta; PUM262054 light magenta; PUK1176 black; PUK250754 black; PUR242158 red (PMS 032); Flex UV Platform; Jet UV Platform; LOK UV Platform; Stretch UV Platform; PUB242359 blue (PMS 3025); PUG249652 green (PMS 347); and PUK1189 black.

In some configurations, the energy curable ink 304 may be in the form of a hybrid composed of energy curable ingredients in an aqueous solution. In some configurations, a multi-stage printing system may be utilized. In some configurations, to improve ink rub-off resistance, ink compositions used herein may contain a wax. Such waxes may include a polyethylene wax emulsion. Addition of a wax to the ink composition may enhance rub resistance by setting up a barrier which inhibits the physical disruption of the ink film after application of the ink to the fibrous sheet. Based on weight percent solids of the total ink composition, addition ranges for the wax may be from about 0.5% solids to 10% solids. An example polyethylene wax emulsion is JONWAX 26 supplied by S.C. Johnson & Sons, Inc. of Racine, Wis.

In some configurations, the energy curable ink 304 may include a solvent. In some examples, solvents and/or solvent blends may be used to achieve or help achieve desired physical properties, surface tension, viscosity, or specific gravity or a combination thereof. Example solvents for ink composition may include, without limitation, alcohols, acetates, ketones, glycol ethers, aromatic hydrocarbons, aliphatic naphthas, water, glycols, and combinations thereof. Alcohols may include ethyl alcohol, isopropyl alcohol, N-propyl alcohol, and blends thereof. Acetates may include ethyl acetate, N-propyl acetate, N-butyl acetate, isopropyl acetate, isobutyl acetate, butyl acetate, and blends thereof. Glycol ethers may include ethylene glycol monopropyl ether, ethylene glycol monobutyl ether, diethylene glycol monomethyl ether, diethylene glycol monopropyl ether, propylene glycol monomethyl ether, polyproylene glycol n-propyl ether, and blends thereof. Some solvents may include dipropylene glycol methyl ether, dipropylene glycol n-butyl ether, propolyene glycol, ethylene glycol, dipropylene glycol, and combinations or blends thereof.

In some configurations, the energy curable ink 304 may be compounded to be printed to meet select physical property ranges. While not wishing to be bound by theory, it is believed certain physical property ranges may affect some characteristics of the printed region 400. For example, the energy curable ink 304 may be configured with a surface tension to promote wetting of the substrate 200 by the energy curable ink 304. In another example, the energy curable ink 304 may be configured with a viscosity that promotes ink penetration into the substrate 200. In yet another example, the energy curable ink 304 may be configured with a specific gravity to promote wetting of the substrate 200 and thereby promoting ink penetration therein.

In some configurations, the energy curable ink 304 may have an ink composition that may have a relatively low surface tension compared to the surface tension of fibers that may make up the substrate 200, such as fibers in a nonwoven, or surfaces 202, 204 of the substrate, so as facilitate wetting by the ink composition. As such, the surface tension may provide desirable ink wetting of the substrate. In one nonlimiting example, the ink composition may have a surface tension as measured in dyne/cm at 25 degrees Celsius, which is numerically less than the surface tension of the fibers or surfaces making up the substrate 200, such as a nonwoven. In yet another example, the ink composition may have a surface tension as measured in dyne/cm at 25 degrees Celsius of less than 30.

In some configurations, the energy curable ink 304 may have an ink composition that may have a viscosity such that ink penetration occurs upon wetting the substrate 200. It is to be appreciated that various factors may influence ink penetration, such as for example, the ink's resistance to flow, thickness, and/or viscosity. In accordance with one example, the ink composition may have a viscosity in the range of 1 to 30 millipascal seconds. The viscosity measurement is done according to ASTM D 2196-99 Test Method A, where a UL adaptor is utilized and the measurements are made as outlined in ASTM D 2196-99, Test Method A at 25° C. and 60 rpm. Shake time and spindle selection are as indicated within the test method.

In some configurations, the energy curable ink 304 may have an ink composition that may have a specific gravity that also promotes wetting of the substrate, such as a nonwoven, and thereby promoting ink penetration therein. An example ink composition may have a specific gravity in the range of 0.830 to 1.050. The specific gravity is measured according to ASTM D 891-95 following Method A and determined at 25° C.

As previously mentioned and as shown in FIGS. 3-6, the printing system 300 includes the light source 308 that directs ultraviolet light 310 onto the substrate 200 to define the illumination zone 312. It is to be appreciated that ultraviolet light 310 may have various wavelengths that may be used to cure the energy curable ink 304. In some configurations, the ultraviolet light 310 may have wavelengths in the range of from about 200 nm to about 400 nm, or from about 300 nm to about 400 nm, reciting for each range every 10 nm increment therein. In nonlimiting examples, energy curable inks may be cured with ultraviolet light having a 365 nm wavelength or a 395 nm wavelength. The energy curable inks 304 may incorporate one or more photoinitiators to trigger the crosslinking polymerization. In some examples, an energy curable ink 304 comprises about 15% or less, or about 10% or less by weight of photoinitiator(s). The type of photoinitiator may affect the wavelength necessary for curing. In some configurations, energy curable inks 304 may be cured using energy dosages of at least about 10 $mJ/cm^2$, or about 2000 $mJ/cm^2$ or less, or about 1000 $mJ/cm^2$ or less, from about 10 $mJ/cm^2$ to about 2000 $mJ/cm^2$, or from about 25 $mJ/cm^2$ to about 1000 $mJ/cm^2$, reciting for each range every 10 $mJ/cm^2$ increment therein.

Figure 4:
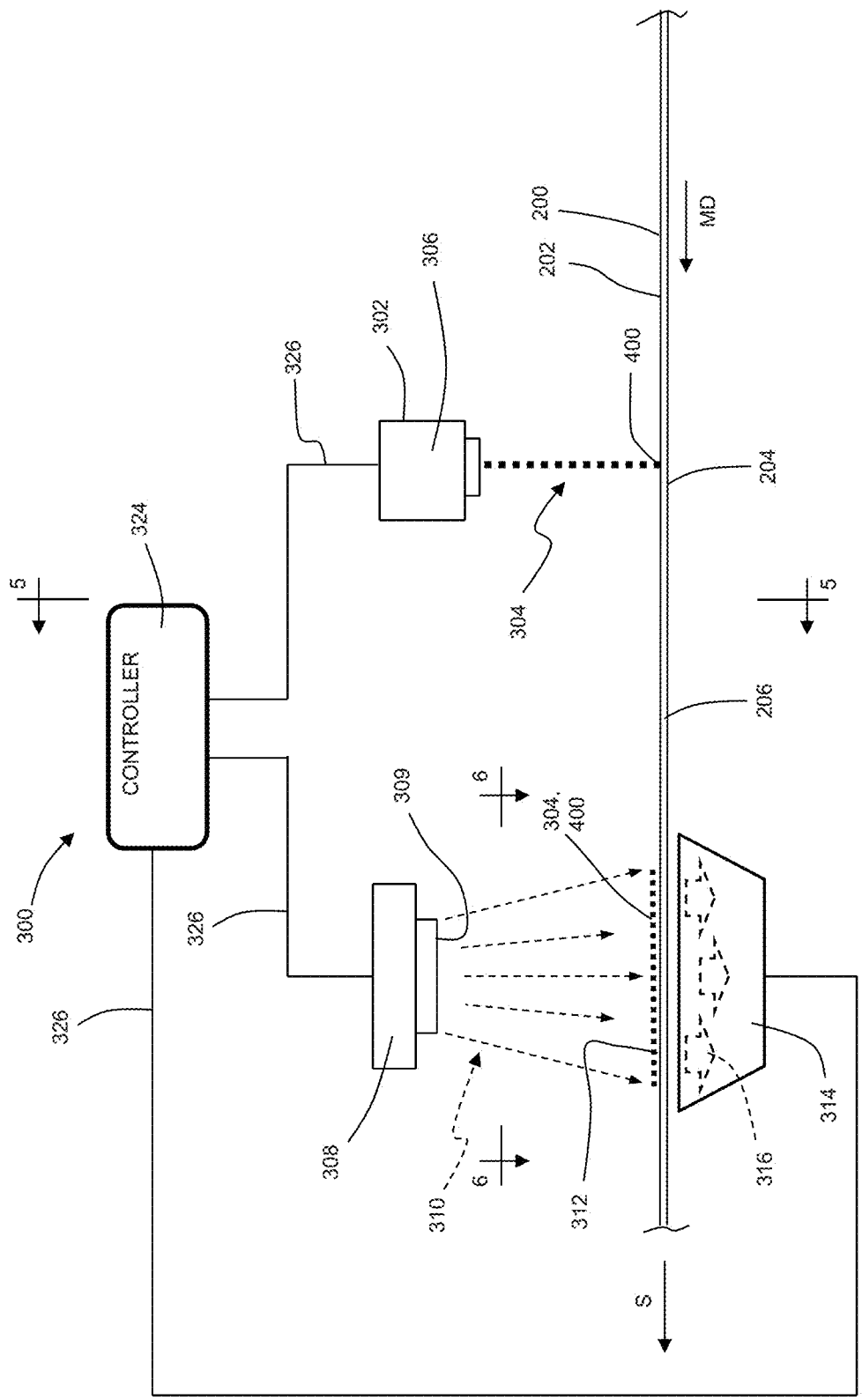
FIG. 4 is a left side view of the substrate and printing system of FIG. 3 showing a cooling apparatus adjacent the substrate.
Figure 5:
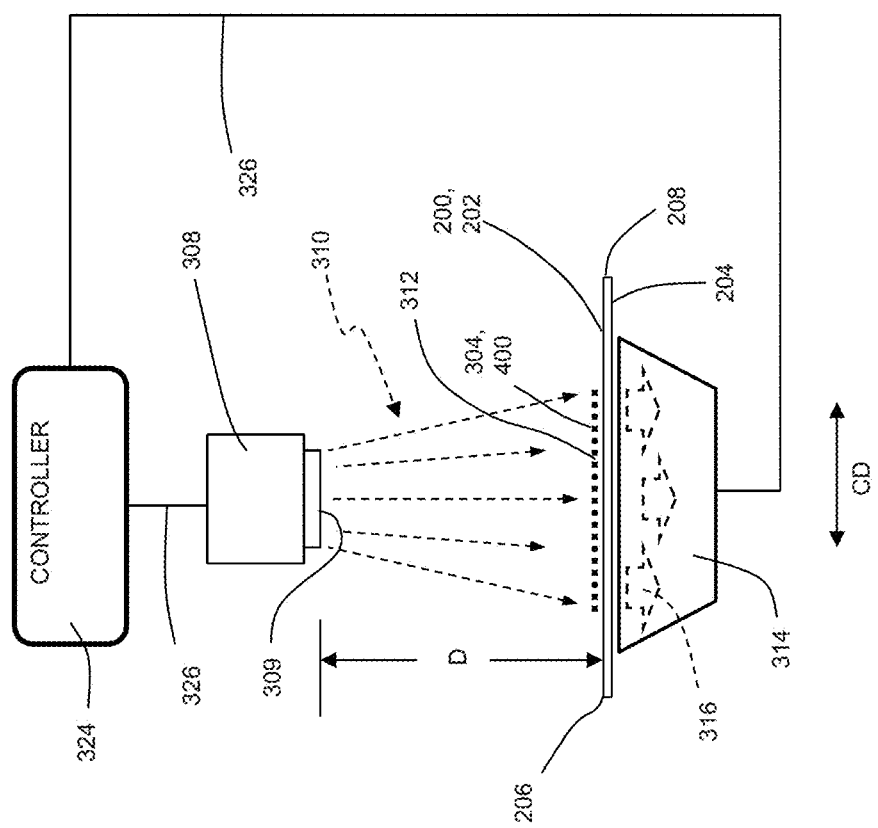
FIG. 5 is a cross sectional view of the substrate and printing system taken along the sectional line 5-5 of FIG. 4.
Figure 6:
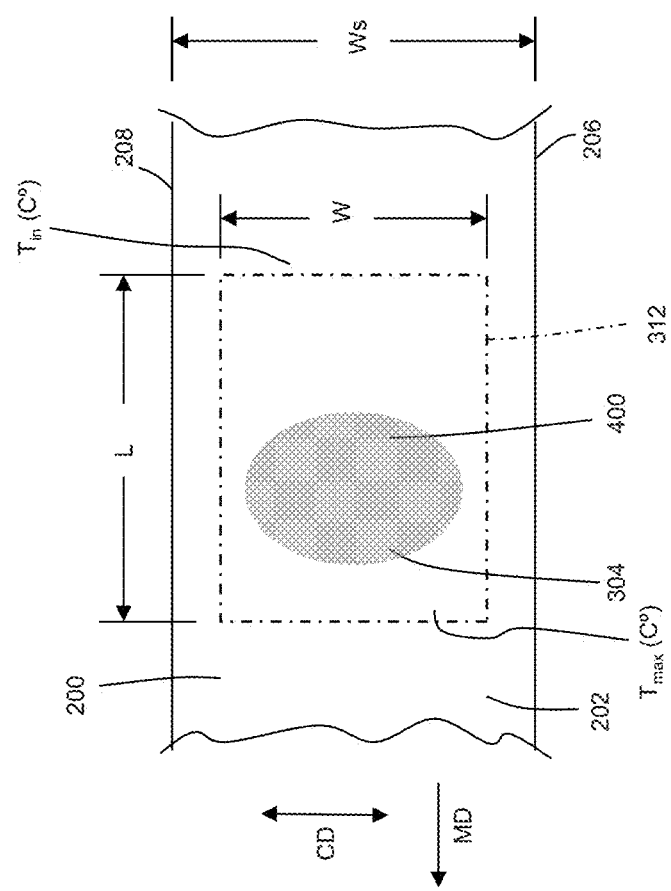
FIG. 6 is a top side view of the advancing substrate taken along the sectional line 6-6 of FIG. 4.

It is to be appreciated that the light source 308 shown in FIGS. 3-5 may be configured in various ways. For example, the light source 308 may include a window 309 that is positioned a distance D from the first surface 202 of the substrate 200. In some configurations, the distance D may be about 2 mm to about 50 mm. In addition, the light source 308 may include one or more lamps that direct ultraviolet light 310 toward the substrate 200 to define the illumination zone 312. In some configurations, the lamps may be configured as LEDs. The light source 308 may also be configured to define illumination zones 312 having various different sizes and/or shapes. As shown in FIG. 6, the illumination zone 312 may extend for length L in the machine direction MD and may extend for a width W in the cross direction CD. In addition, the substrate 200 may define a width Ws in the cross direction CD between the first side edge 206 and the second side edge 208, and the width W of the illumination zone 312 may be greater than, equal to, or less than the width Ws of the substrate 200. It is also to be appreciated that the light source 308 may be configured such that light in the illumination zone 312 may have the same wavelength or different wavelengths along the length and/or width of the illumination zone 312. In addition, the light source 308 may be configured such that light in the illumination zone 312 may have the same intensity or different intensities along the length and/or width of the illumination zone 312. It should also be appreciated that the printing system 300 may include additional options associated with the curing of energy curable inks. For example, the printing system 300 may be configured such that the energy curable ink 304 advances through a nitrogen atmosphere during the curing process.

As discussed above with reference to FIGS. 3-6, the printing station 302 deposits energy curable ink 304 onto the first surface 202 of the advancing substrate 200 to define a printed region 400. In turn, the substrate 200 advances the printed region 400 through the illumination zone 312 where ultraviolet light 310 traveling from the light source 308 cures the energy curable ink 304 on the substrate 200. As previously mentioned, ultraviolet light 310 in the illumination zone 312 is also absorbed by the substrate 200 and converted into heat energy. If the substrate 200 is excessively heated, the substrate 200 may become damaged. Thus, the printing system 300 may include a cooling apparatus 314 that removes heat energy 316 from the substrate 200 before, during, and/or after the printed region 400 advances through the illumination zone 312.

It is to be appreciated that the printing systems 300 herein may include one or more cooling apparatuses 314 that may be configured in various ways. For example, the cooling apparatus 314 may include a heat exchanger, such as a heat sink. In some examples, the cooling apparatus 314 may include a device, such as a fan or blower, moves air or other gas along the first surface 202 and/or second surface 204 the substrate 200 to remove heat energy from the substrate 200 with convection. Although the cooling apparatus 314 schematically represented in FIGS. 4 and 5 is adjacent the second surface 204 of the substrate 200, it is to be appreciated that the cooling apparatus 314 may be configured with components that are in close proximity with or in contact with the first surface 202 and/or the second surface 204 of the substrate 200.

Figure 7:
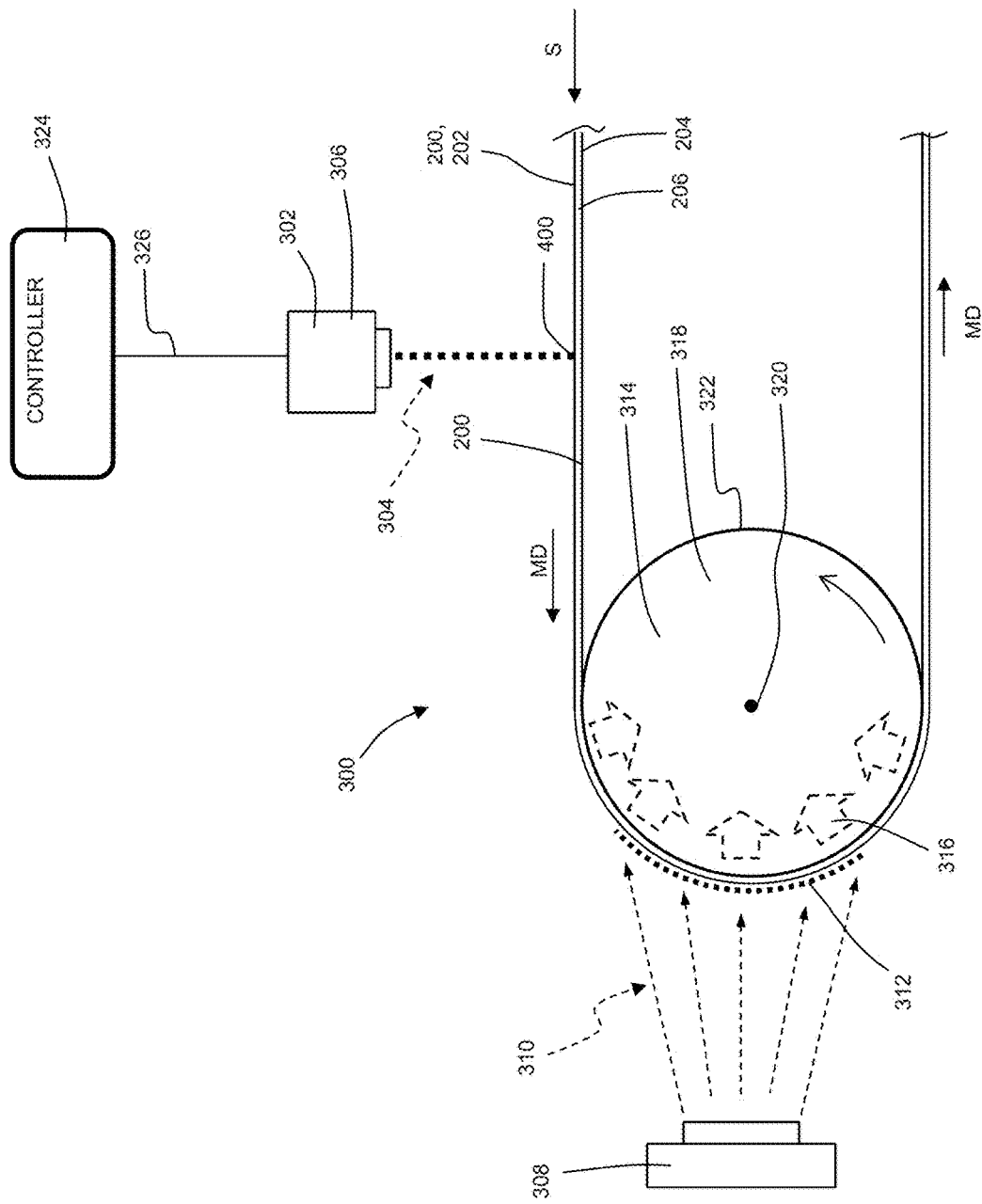
FIG. 7 is a schematic side view of a printing system and an advancing substrate partially wrapped around a chill roll.

FIG. 7 shows a configuration where the cooling apparatus comprises a chill roll 318 adapted to rotate around an axis of rotation 320. The chill roll 318 includes an outer circumferential surface 322. During operation, printing station deposits energy curable ink 304 onto the first surface 202 of the substrate 200 to create a printed region 400. The substrate 200 advances from the printing station 302 and is partially wrapped onto the chill roll 318. More particularly, the second surface 204 of the substrate 200 is partially wrapped onto the outer circumferential surface 322 of the rotating chill roll 318. The light source 308 directs ultraviolet light 310 toward the substrate 200 while wrapped onto the chill roll 318 to define an illumination zone 312 on the first surface 202 of the substrate 200. In turn, the chill roll 318 removes heat energy 316 from the substrate 200. Although the printing station 302 is illustrated as being positioned so as to print the substrate 200 before the printed region 400 advances onto the chill roll 318, it is to be appreciated the that printing station 302 could be configured to print the substrate 200 while the substrate 200 is positioned on the outer circumferential surface 322 of the chill roll 318. It is to be appreciated that various configurations of chill rolls may be used, such as for example, chill rolls available from Menges Roller Company in Wauconda, Ill.

As discussed above, during operation, the printing station 302 deposits energy curable ink 304 on the first surface 202 of the substrate 200 to define the printed region 400. As such, the printed region 400 includes an ink basis weight, IBW (gsm), that requires energy, Ec (J/m$^2$), to cure the energy curable ink 304. "Ink Basis Weight" (IBW) as used herein is the weight per unit area of a sample reported in grams per square meter (gsm) and is measured according to the Ink Basis Weight Test Method described herein. In the illumination zone 312, the ultraviolet light 310 comprises an intensity I (W/m$^2$) at the first surface 202 of the substrate 200. Thus, the energy curable ink 304 may need to be subjected to the intensity I (W/m$^2$) for a period of time so as to reach the energy level Ec (J/m$^2$). As discussed above, the substrate 200 advances in the machine direction MD at a speed S (m/s), and the illumination zone 312 extends in the machine direction for a length (L). In turn, energy curable ink 304 of the printed region 400 advances through the illumination zone 312 at speed S (m/s), and thus, the time to advance through the illumination zone 312 is equal to: L (m)/S (m/s). Thus, the intensity and time needed to cure energy curable ink 304 advancing through the illumination zone 312 should be equal to or greater than the energy required to cure the energy curable ink 304 applied to the substrate 200 with a particular ink basis weight, and may be expressed by the following equation:

$$[I(W/m^2) \times L(m)/S(m/s)] \geq Ec(J/m^2)].$$

It is to be appreciated that the printed regions 400 herein may have various ink basis weights. For example, in some configurations, the printed region 400 may have an ink basis weight of at least about 0.5 gsm, or at least about 1.0 gsm, or at least about 1.5 gsm, or from about 1 gsm to about 7 gsm, or about 1.5 gsm to about 5.5 gsm, or about 6 gsm or less. It is also to be appreciated that the printed regions 400 may have various print resolutions. For example, the printed region 400 may have a print resolution of at least about 64 dpi, or at least about 100 dpi, or from about 64 dpi to about 1200 dpi, or from about 200 to about 400 dpi, or about 400 dpi or less, reciting for each range every 1 dpi increments therein and all ranges formed therein or thereby in the cross machine direction of the substrate 200, which in some configurations corresponds to the lateral direction of the substrate. In some examples, the printed region 400 may have a print resolution of at least about 10 dpi, or about 6000 dpi or less, or about 1500 dpi or less, or about 100 dpi or less, or from about 10 dpi to about 6000 dpi, reciting for each range every 1 dpi increments therein and all ranges formed therein or thereby in the machine direction of the substrate 200, which in some configurations corresponds to the longitudinal direction of the substrate 200. The energy curable ink 304 may also comprise a colorant. In some configurations, the energy curable ink 304 comprises cyan, magenta, yellow, black, or combinations thereof. The energy curable ink 304 may also be disposed on at least 5%, or at least 10%, or at least 20%, or at least 25%, or from about 10% to about 90% of the surface based on the total area of the surface as determined by the Percent Printed Color Area Test Method herein.

As previously discussed, the substrate 200 absorbs energy used to the cure the energy curable ink 304 in the illumination zone 312, which in turn, may cause the temperature of substrate 200 to increase. For example, in some configurations where printing is performed online during an article assembly process, energy curable ink 304 may be required to advance past the ultraviolet light 310 in the illumination zone 312 at a relatively high rate of speed S (m/s). As such, the time during which energy curable ink 304 is exposed to ultraviolet light 310 may be relatively short. As discussed above, in order to cure the energy curable ink 304 in a relatively short period of time, the intensity of the ultraviolet light 310 may need to be increased to relatively high levels. However, if the intensity is too high over a period of time, the heat energy created in the substrate 200 from the ultraviolet light 310 may destroy and/or damage the advancing substrate 200.

To help prevent damage to the substrate 200 during the curing process, the printing system 300 may be configured to maintain the temperature of the substrate 200 at or below an onset temperature, $T_{onset}$ (C°). As used herein, the onset temperature, $T_{onset}$ (C°), of a substrate is determined by the Differential Scanning calorimetry Test Method herein. In turn, the printing system 300 may be configured such that the ultraviolet light 310 heats the substrate 200 from an initial temperature $T_{in}$ (C°) entering the illumination zone 312 to a maximum temperature $T_{max}$ (C°), wherein $T_{max}$ (C°)≤$T_{onset}$ (C°) in the illumination zone 312, such as schematically represented in FIG. 6. In some configurations, the maximum temperature $T_{max}$ (C°) of the substrate 200 in the illumination zone 312 may be maintained below the onset temperature, $T_{onset}$ (C°) by controlling the speed S (m/s) at which the printed region 400 advances through the illumination zone at a speed S (m/s) and/or by controlling the length L (m) and/or width W (m) of the illumination zone 312 so as to control the time at which the energy curable ink 400 is exposed to the ultraviolet light 310 having an intensity I (W/m$^2$) in the illumination zone 312. In addition, the intensity I (W/m$^2$) ultraviolet light 310 in the illumination zone 312 may be controlled.

In some configurations such as described above with reference to FIGS. 3-7, the printing system 300 may include one or more cooling apparatuses 314 discussed above to remove heat energy 316 from the substrate 200 to help maintain the maximum temperature $T_{max}$ (C°) of the substrate 200 in the illumination zone 312 below the onset temperature, $T_{onset}$ (C°). As such, the one or more cooling apparatuses 314 may be configured to remove heat energy 316 from the substrate 200 while curing the energy curable ink 304 advancing through the illumination zone 312. In some configurations, one or more cooling apparatuses 314 may also be configured to remove heat energy 316 from the substrate 200 before and/or after energy curable ink 304 advances through the illumination zone 312. As such, one or more cooling apparatuses 314 may also be configured to remove heat energy 316 from the substrate 200 to so as reduce the initial temperature $T_{in}$ (C°) of the substrate 200 entering the illumination zone 312.

It is to be appreciated that the printing system 300 herein may also include various additional features. For example, as previously mentioned, the printing system 300 may be configured to print off-line or interact with and/or be configured as a unit operation of a converting line. In some configurations of the printing system 300, the printer 306, the light source 308, and/or the cooling apparatus 314 may be arranged adjacent the advancing substrate 200, and the printer 306, the light source 308, and/or the cooling apparatus 314 may interface and communicate with a controller 324. The controller 324 may be adapted to control the operation of the printer, light source, cooling apparatus, and/or may allow an operator to manually program the type of graphics to be printed. For example, the printing system 300 may be configured with various features, such as available on the XD070 Multi-Color Industrial Ink Jet unit available from Pad Print Machinery of Vermont. In some configurations, the printing system 300 may be configured to interface with other computerized systems and/or networks that may automatically program or command the printing system to print various graphics based on various input, such as sales orders from customers. It is to be appreciated that the controller 324 may be configured in various ways. For example, the controller 324 may be in the form of a personal computer (PC) or a central processing unit (CPU). The controller 324 may also be configured to monitor and affect various operations on a converting line. For example, the controller 324 may send various types of control commands to the converting line based on communications with sensors adjacent the converting line.

It is to be appreciated that the controller 324 may also be configured to communicate with one or more computer systems, such as for example, a programmable logic controller (PLC) and/or personal computer (PC) running software and adapted to communicate on an EthernetIP network. Some embodiments may utilize industrial programmable controllers such as the Siemens S7 series, Rockwell ControlLogix, SLC or PLC 5 series, or Mitsubishi Q series. The aforementioned embodiments may use a personal computer or server running a control algorithm such as Rockwell SoftLogix or National Instruments Labview or may be any other device capable of receiving inputs from sensors, performing calculations based on such inputs and generating control actions through servomotor controls, electrical actuators or electro-pneumatic, electrohydraulic, and other actuators. In some configurations, process and product data may be stored directly in the aforementioned computer systems or may be located in a separate data historian. In some embodiments, the historian is a simple data table in the controller. In other embodiments, the historian may be a relational or simple database. Common historian applications include Rockwell Automation Factory Talk Historian, General Electric Proficy Historian, OSI PI, or any custom historian that may be configured from Oracle, SQL or any of a number of database applications. It is also to be appreciated that the controller 324 may be configured to communicate with various types of controllers and inspection sensors configured in various ways and with various algorithms to provide various types of data and perform various functions, for example, such as disclosed in U.S. Pat. Nos. 5,286,543; 5,359,525; 6,801,828; 6,820,022; 7,123,981; 8,145,343; 8,145,344; and 8,244,393; and European Patent No. EP 1528907 B1, all of which are incorporated by reference herein.

As shown in FIGS. 3-5, the printer 306, light source 308, and/or cooling apparatus 314 may be in communication with the controller 324 through a communication network 326. As such, it is to be appreciated that the controller 324 may be physically located near the advancing substrate 200, printing station 302, the light source 308, and/or cooling apparatus 314 and/or may be located at another location and in communication with the printer 306, the light source 308, and/or the cooling apparatus 314 via a wired and/or wireless network 326. In some embodiments, the communication network 326 is configured as a non-deterministic communication network, such as for example, Ethernet or Ethernet IP (industrial protocol) communication network.

When printing on fibrous substrates, such as nonwovens, the printed energy curable ink 304 may penetrate into the substrate 200. In some instances, some of the energy curable ink 304 may flow or migrate entirely through the substrate 200 from the first surface 202 to the second surface 204. In addition, a portion of the ultraviolet light 310 traveling from the light source 308 may also travel through substrate 200 and away from the second surface 204 of the substrate 200. As such, the printing systems 300 herein may include a reflective device, such as a mirror, that reflects ultraviolet light 310 traveling from the second surface 204 of the substrate 200 back toward the second surface 204 of the substrate 200 to cure energy curable ink 304 that may have flowed or migrated entirely through the substrate 200 from the first surface 202 to the second surface 204. In some configurations, the cooling apparatus 314 may be configured to reflect the ultraviolet light 310 as described above. For example, the outer circumferential surface 322 of the chill roll 318 shown in FIG. 7 may be configured to reflect ultraviolet light 310 traveling through the substrate 200 and back toward the second surface 204 of the substrate 200 to cure energy curable ink 304 that may have flowed or migrated entirely through the substrate 200 from the first surface 202 to the second surface 204. Example configurations of such reflective devices are disclosed in U.S. Provisional patent application entitled "Method and Apparatus for Curing Inks Printed on Fibrous Absorbent Article Components,".

It is also to be appreciated that the printing systems 300 herein may be configured to print printed regions 400 at desired print resolutions on a substrate 200, wherein the printed regions may form graphics G, such as discussed above with reference to absorbent articles assembled with various components that may be printed off-line, before assembly, or on-line, as part of the assembly process. Thus, in the context of the previous discussion, the printing system 300 herein may be used to print substrates and components of an absorbent article 100, either off-line or on-line. For example, the printing system 300 herein may be utilized to print printed regions to form graphics on any of the topsheet 138; backsheet 136; absorbent core 140; leg cuffs 156; waist feature 158; side panels 104, 106, 108, 110; connection zones 168; fastening elements 162, 166, and/or belts before or during the manufacture of an absorbent article 100.

Ink Basis Weight Test Method

Remove the printed substrate from the product without damaging the printed substrate.

Punch out a material swatch with a known area (e.g. 1 cm/\2 punch) of printed material where you would like to determine the ink basis weight.

Punch out the same printed area on 100 different products. Combine all 100 material swatches and weigh. Record the total weight in grams to 2 decimal places of the 100 printed material swatches.

Punch out a material swatch with a known area (e.g. 1 cm/\2 punch) of the same substrate as the printed material, but this time in an area without any ink on it.

Punch out the same non-printed area on 100 different products.

Combine all 100 material swatches and weigh. Record the total weight in grams to 2 decimal places of the 100 non-printed material swatches.

Use the equation below to calculate the ink basis weight for the given printed area.

$$\text{Ink Basis Weight} = \frac{\text{Printed Material Mass}}{\text{Printed Punch Area} \times \text{\# of Printed Repeats}} - \frac{\text{Non-Printed Material Mass}}{\text{Non-Printed Punch Area} \times \text{\# of Non-Printed Repeats}}$$

Percent Printed Color Area Test Method

Percent Printed Color Area is used to determine the amount of printed color coverage on a component layer of an absorbent article images acquired using a flatbed scanner.

The scanner is capable of scanning in reflectance mode at a resolution of 150 dpi and 24 bit color (a suitable scanner is an Epson Perfection V750 Pro from Epson America Inc., Long Beach Calif. or equivalent). The scanner is interfaced with a computer running an image analysis program (a suitable program is ImageJ v. 1.50 or equivalent, National Institute of Health, USA). The specimen images are distance calibrated against an acquired image of a ruler certified by NIST. The resulting image is then analyzed using the image analysis program to identify the boundaries of the printed color regions and calculate the percent printed color area.

Remove the printed substrate of interest from an absorbent article using cryogenic spray (such as Cyto-Freeze, Control Company, Houston Tex.) or other means as needed to separate the substrate from other components of the article and avoid any longitudinal and lateral distortion of the specimen. Five replicates of this specimen layer, obtained from five substantially similar absorbent articles, are prepared for analysis. Precondition the specimens at about 23° C.±2° C. and about 50%±2% relative humidity for 2 hours prior to testing.

Place the ruler on the center of the scanner bed, oriented parallel to the sides of the scanner glass, and close the lid. Acquire a calibration image of the ruler in reflectance mode at a resolution of 150 dpi (approximately 5.9 pixels per mm) and 24 bit color. Save the calibration image as an uncompressed TIFF format file. Lift the lid and remove the ruler. After obtaining the calibration image, all specimens are scanned under the same conditions and measured based on the same calibration file. Next, place the specimen onto the center of the scanner bed, lying flat, with the color printed facing surface of the specimen facing the scanner's glass surface. Cover the specimen with a white background (in this test method white is defined as having $L^*>94$, $-2<a^*<2$, and $-2<b^*<2$ based on the standard CIE $L^*a^*b^*$ color space) and close the lid. Acquire and save a scanned image of the specimen layer. If the size of the specimen layer exceeds the available scanning area, obtain multiple scans covering the entire specimen layer and digitally stitch them together into a single image for analysis. Scan the remaining four replicates in like fashion.

Open the calibration image file in the image analysis program and perform a linear distance calibration using the imaged ruler. This distance calibration scale will be applied to all subsequent specimen images prior to analysis. Open a specimen image in the image analysis program and set the distance scale. Using the image analysis program, identify and define the boundaries of any printed color regions in the image of the specimen layer. Identification of color region boundaries should be performed with the intent of defining them as they would be discerned by a human viewer under standard lighting conditions with the unaided eye if the layer were being viewed face on in a flat configuration at approximately an arm's length distance. For example, intra-dot spaces commonly associated with ink-jet printing are included within that ink region, because they are perceived as part of that printed region by a typical viewer without magnification.

Calculate the area of each of the individual printed color regions within the image to the nearest 0.1 mm$^2$. Calculate the total area of printed color by summing up the areas of the individual printed color regions. Divide the total area of the printed color regions by the area of the entire specimen layer and multiply by 100. Record this value as the printed color percent area to the nearest 0.1%. In like fashion, analyze the remaining four specimen images. Calculate and report the average printed color percent area to the nearest 0.1% for the five replicates.

Differential Scanning Calorimetry Test Method

The Differential Scanning calorimetry measurement is run according to ASTM 3418-15 with the following specifications: All testing is performed in a room controlled at 23° C.±3° C. and 50%±2% relative humidity. Condition all samples for two hours prior to specimen preparation and testing. Prepare three (3) replicate sealed test specimens by cutting them from a non-printed area of the nonwoven, film, laminate, or substrate adjunct to the printed area to a weight of 5-10 mg, but not exceeding a circular area with 2.5 mm in diameter. Run the method as specified in ASTM 3418-15 with a ramp of 20° C./min up to 400° C. Record the $T_{eim}$=melting extrapolated onset temperature in ° C. for the first heat for each of the three test specimens Average the three $T_{eim}$ values and report as the onset temperature, $T_{onset}$ (C°), to the nearest degree C.

This application claims the benefit of U.S. Provisional Application No. 62/467,995, filed on Mar. 7, 2017, the entirety of which is incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for printing, the method comprising:
   providing a substrate extending in a machine direction, the substrate comprising a first surface and an opposing second surface and defining a width in a cross direction;
   depositing energy curable ink onto the first surface of the substrate to define a printed region;
   directing ultraviolet light from a light source onto the first surface of the substrate to define an illumination zone extending for a length, L (m), in the machine direction on the first surface of the substrate;
   advancing the printed region through the illumination zone;
   curing the energy curable ink advancing through the illumination zone with ultraviolet light traveling from the light source, wherein a portion of the ultraviolet light travels through the substrate and away from the second surface of the substrate;

reflecting the ultraviolet light traveling from the second surface of the substrate back toward the second surface of the substrate; and removing heat energy from the substrate.

2. The method of claim 1, wherein removing heat energy further comprises partially wrapping the substrate onto a chill roll.

3. The method of claim 2, wherein partially wrapping the substrate onto the chill roll further comprises positioning the second surface of the substrate onto an outer circumferential surface of the chill roll.

4. The method of claim 2, wherein the chill roll is rotatable about an axis, and wherein advancing the printed region further comprises rotating the chill roll.

5. The method of claim 2, wherein the chill roll comprises a reflective outer surface, and wherein the ultraviolet light traveling from the second surface of the substrate is reflected back toward the second surface of the substrate by the reflective outer surface of the chill roll.

6. The method of claim 1, wherein removing heat energy from the substrate is performed while curing energy curable ink advancing through the illumination zone.

7. The method of claim 1, wherein removing heat energy from the substrate is performed before curing energy curable ink advancing through the illumination zone.

8. The method of claim 1, wherein the substrate comprises a nonwoven material.

9. The method of claim 1, wherein the ultraviolet light comprises an intensity I (W/m$^2$) at the first surface of the substrate in the illumination zone, wherein the printed region comprises an ink basis weight, IBW (gsm), that requires energy, Ec (J/m$^2$), to cure the energy curable ink, and wherein the printed region is advanced through the illumination zone at a speed, S (m/s), such that [I (W/m$^2$) x L (m)/S (m/s)]≥Ec (J/m$^2$)].

10. The method of claim 1, wherein the ultraviolet light comprises a plurality of different wavelengths.

11. The method of claim 1, wherein the light source comprises a plurality of LEDs arranged to extend for a length in the machine direction.

12. The method of claim 1, wherein the energy curable ink comprises a first color and a second color, wherein the first color is different from the second color.

13. A method for printing, the method comprising:
providing a nonwoven substrate extending in a machine direction, the substrate comprising a first surface and an opposing second surface and defining a width in a cross direction, the substrate comprising a melting onset temperature $T_{onset}$ (C°);

depositing energy curable ink onto the first surface of the nonwoven substrate to define a printed region;

directing ultraviolet light from a light source onto the first surface of the nonwoven substrate to define an illumination zone extending for a length, L (m), in the machine direction on the first surface of the substrate;

advancing the printed region through the illumination zone at a speed, S (m/s), such that the ultraviolet light heats the nonwoven substrate from an initial temperature $T_{in}$(C°) entering the illumination zone to a maximum temperature $T_{max}$ (C°), wherein $T_{max}$(C°)<$T_{onset}$ (C°) in the illumination zone; and curing the energy curable ink advancing through the illumination zone with ultraviolet light traveling from the light source.

14. The method of claim 13, wherein the ultraviolet light comprises an intensity I (W/m$^2$) at the first surface of the nonwoven substrate in the illumination zone, and wherein the printed region comprises an ink basis weight, IBW (gsm), that requires energy, Ec (J/m$^2$), to cure the energy curable ink; and wherein [I (W/m$^2$) x L (m)/S (m/s)]>Ec (J/m$^2$)].

15. The method of claim 13, further comprising removing heat energy from the nonwoven substrate.

16. The method of claim 15, wherein removing heat energy from the nonwoven substrate is performed before curing the energy curable ink advancing through the illumination zone.

17. The method of claim 15, wherein removing heat energy from the nonwoven substrate is performed while curing the energy curable ink advancing through the illumination zone.

18. An apparatus for printing a substrate extending in a machine direction, the substrate comprising a first surface and an opposing second surface and defining a width in a cross direction, the apparatus comprising:
a supply of energy curable ink;
a printing station positioned to deposit energy curable ink from the supply onto the first surface of the substrate;
a curing apparatus for curing the energy curable ink on the substrate, the curing apparatus comprising: a light source positioned to direct ultraviolet light toward the first surface of the substrate at a location downstream in the machine direction from the printing station, wherein the ultraviolet light source comprises a wavelength and wherein a portion of the ultraviolet light travels through the substrate and away from the second surface of the substrate, and
a chill roll comprising an outer circumferential surface positioned to support the second surface of the substrate, wherein the chill roll is adapted to remove heat energy imparted to the substrate from the curing apparatus; and
a reflective device positioned to reflect the ultraviolet light traveling from the second surface of the substrate back toward the second surface of the substrate.

19. The apparatus of claim 18, wherein the reflective device comprises an outer surface of the chill roll.

20. The method of claim 1, wherein the substrate comprises a melting onset temperature $T_{onset}$(C°), and wherein the printed region is advanced through the illumination zone at a speed, S (m/s), such that the ultraviolet light heats the substrate from an initial temperature $T_{in}$ (C°) entering the illumination zone to a maximum temperature $T_{max}$(C°), wherein $T_{max}$ (C°)<$T_{onset}$(C°) in the illumination zone.

* * * * *